United States Patent
Diamond et al.

(10) Patent No.: US 11,141,492 B2
(45) Date of Patent: Oct. 12, 2021

(54) ANTICANCER COMBINATIONS

(71) Applicant: City of Hope, Duarte, CA (US)

(72) Inventors: Don J. Diamond, Glendora, CA (US);
Edwin Manuel, Pomona, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 14/978,590

(22) Filed: Dec. 22, 2015

(65) Prior Publication Data

US 2016/0184456 A1 Jun. 30, 2016

Related U.S. Application Data

(63) Continuation of application No. PCT/US2014/045086, filed on Jul. 1, 2014.

(60) Provisional application No. 61/842,749, filed on Jul. 3, 2013.

(51) Int. Cl.
| | | |
|---|---|---|
| A61K 48/00 | (2006.01) | |
| A61K 38/47 | (2006.01) | |
| A61K 45/06 | (2006.01) | |
| A61K 35/74 | (2015.01) | |
| A61K 31/337 | (2006.01) | |
| A61K 31/7068 | (2006.01) | |
| C12N 15/113 | (2010.01) | |
| A61P 35/00 | (2006.01) | |
| A61K 31/713 | (2006.01) | |

(52) U.S. Cl.
CPC ........ A61K 48/0025 (2013.01); A61K 31/337 (2013.01); A61K 31/7068 (2013.01); A61K 31/713 (2013.01); A61K 35/74 (2013.01); A61K 38/47 (2013.01); A61K 45/06 (2013.01); A61P 35/00 (2018.01); C12N 15/1137 (2013.01); C12Y 302/01035 (2013.01); C12N 2310/11 (2013.01); C12N 2320/31 (2013.01); C12N 2320/32 (2013.01); Y02A 50/30 (2018.01)

(58) Field of Classification Search
None
See application file for complete search history.

(56) References Cited

U.S. PATENT DOCUMENTS

| | | |
|---|---|---|
| 6,573,099 B2 | 6/2003 | Graham |
| 7,767,429 B2 | 8/2010 | Bookbinder et al. |
| 7,829,081 B2 | 11/2010 | Bookbinder et al. |
| 7,846,431 B2 | 12/2010 | Bookbinder et al. |
| 7,871,607 B2 | 1/2011 | Bookbinder et al. |
| 8,105,586 B2 | 1/2012 | Bookbinder et al. |
| 8,202,517 B2 | 6/2012 | Bookbinder et al. |
| 8,257,699 B2 | 9/2012 | Bookbinder et al. |
| 8,431,380 B2 | 4/2013 | Bookbinder et al. |
| 8,450,470 B2 | 5/2013 | Bookbinder et al. |
| 2002/0160393 A1 | 10/2002 | Symonds et al. |
| 2003/0027783 A1 | 2/2003 | Zernicka-Goetz |
| 2005/0112141 A1* | 5/2005 | Terman ............ A61K 39/0011 424/192.1 |
| 2009/0123367 A1* | 5/2009 | Bookbinder ........ A61K 38/47 424/1.49 |
| 2009/0208534 A1 | 8/2009 | Xu et al. |
| 2010/0239546 A1 | 9/2010 | Fruehauf et al. |
| 2012/0294830 A1 | 11/2012 | Bookbinder et al. |

FOREIGN PATENT DOCUMENTS

| | | | |
|---|---|---|---|
| JP | 2011-519361 A | 7/2011 | |
| WO | WO-99/07409 A1 | 2/1999 | |
| WO | WO-99/32619 A1 | 7/1999 | |
| WO | WO-00/01846 A2 | 1/2000 | |
| WO | WO-00/01846 A3 | 1/2000 | |
| WO | WO-00/44895 A1 | 8/2000 | |
| WO | WO-00/44914 A1 | 8/2000 | |
| WO | WO-01/29058 A1 | 4/2001 | |
| WO | WO-01/36646 A1 | 5/2001 | |
| WO | WO 2005018332 A1 * | 3/2005 | ............ C12N 1/20 |
| WO | WO-2007/095387 A2 | 8/2007 | |
| WO | WO-2007/095387 A3 | 8/2007 | |
| WO | WO-2007/095387 A8 | 8/2007 | |
| WO | WO-2008/036825 A2 | 3/2008 | |
| WO | WO-2008/036825 A3 | 3/2008 | |
| WO | WO-2009/128917 A2 | 10/2009 | |

(Continued)

OTHER PUBLICATIONS

BLAST sequence alignment software program (at Internet site: https://blast.ncbi.nlm.nih.gov/Blast.cgi). Information downloaded from the internet on May 25, 2017. GenBank accession No. CCSBHm_00014029 for STAT3 mRNA.*

Huang, T-Y. et al. 1999. ACNU, MTX and 5-FU penetration of rat brain tissue and tumors. Journal of Neuro-Oncology 45: 9-17. specif. pp. 9, 12.*

(Continued)

*Primary Examiner* — Lynn Y Fan
*Assistant Examiner* — Sharon M. Papciak
(74) *Attorney, Agent, or Firm* — Mintz, Levin, Cohn, Ferris, Glovsky and Popeo, P.C.

(57) ABSTRACT

Provided herein, inter alia, are compositions and kits comprising a bacterial cell and a tumor penetrating agent. Also provided are methods of treating cancer in a subject including the step of administering to the subject an effective amount of a bacterial cell and a tumor penetrating agent. Provided are methods of stimulating an immune system in a subject. The methods include administering to the subject an effective amount of a bacterial cell and a tumor penetrating agent. Also provided are methods of enhancing delivery of an anti-cancer agent to a tumor cell including the step of contacting the tumor cell with a bacterial cell, a tumor penetrating agent and an anti-cancer agent.

14 Claims, 14 Drawing Sheets

Specification includes a Sequence Listing.

(56) References Cited

FOREIGN PATENT DOCUMENTS

| WO | WO-2009/128917 A3 | 10/2009 |
|---|---|---|
| WO | WO-2012/149364 A1 | 11/2012 |

OTHER PUBLICATIONS

Cherayil, B.J. et al. 2000. *Salmonella enterica* serovar typhimurium-dependent regulation of inducible nitric oxide synthase expression in macrophages by invasins SipB, SipC, and SipD and effector SopE2. Infection and Immunity 68(10): 5567-5574. specif. p. 5567.*

Torchilin, V.P. 2005. Recent advances with liposomes as pharmaceutical carriers. Nature Reviews/Drug Discovery 4: 145-160. specif, p. 147, 148.*

Wirth, M. et al. 2009. Strategies to improve drug delivery in bladder cancer therapy. Expert Opinion on Drug Delivery 6(7): 727-744. specif, p. 727, 728.*

Morrissey, D. et al. 2010. Tumour targeting with systemically administered bacteria. Current Gene Therapy 10: 3-14. specif, pp. 3, 5, 9, 10.*

Rotta, G. et al. 2008. Contrasting roles of SPARC-related granuloma in bacterial containment and in the induction of anti-*Salmonella typhimurium* immunity. Journal of Experimental Medicine 205: 657-667. specif. p. 665.*

Altschul, S.F. et al. (Sep. 1, 1977). "Gapped BLAST and PSI-BLAST: a new generation of protein database search programs," *Nuc Acids Res* 25(17):3389-3402.

Batzer, M.A. et al. (Sep. 25, 1991). "Enhanced evolutionary PCR using oligonucleotides with inosine at the 3'-terminus," *Nucleic Acids Res* 19(18):5081.

Berge, S.M. et al. (Jan. 1977). "Pharmaceutical salts," *J Pharm Sci* 66(1):1-19.

Fabani, M.M. et al. (Feb. 2008, e-published Dec. 11, 2007). "miR-122 targeting with LNA/2'-O-methyl oligonucleotide mixmers, peptide nucleic acids (PNA), and PNA-peptide conjugates," *RNA* 1492):336-346.

Blache, C.A. et al. (Dec. 15, 2012, e-published Oct. 22, 2012). "Systemic delivery of *Salmonella typhimurium* transformed with IDO shRNA enhances intratumoral vector colonization and suppresses tumor growth," *Cancer Res* 72(24):6447-6456.

International Search Report dated Nov. 6, 2014, for PCT Application No. PCT/US2014/045086, filed Jul. 1, 2014, 4 pages.

Kloosterman, W.P. et al. (Aug. 2007). "Targeted inhibition of miRNA maturation with morpholinos reveals a role for miR-375 in pancreatic islet development," PLos Biol 5(8):e203.

Kohno, M. et al. (1994). "Effects of hyaluronidase on doxorubicin penetration into squamous carcinoma multicellular tumor spheroids and its cell lethality," *J Cancer Res Clin Oncol* 120(5);293-297.

Kozono, S. et al. (Apr. 1, 2013, e-published Jan. 24, 20130. "Pirfenidone inhibits pancreatic cancer desmoplasia by regulating stellate cells," *Cancer Res* 73(7):2345-2356.

Leicher, T. et al. (Dec. 25, 1998). "Coexpression of the KCNA3B gene product with Kv1.5 leads to a novel A-type potassium channel," *J Biol Chem* 273(52):35095-35101.

MacEwan, S.R. et al. (Jan.-Feb. 2013, e-published Sep. 13, 2012). "Harnessing the power of cell-penetrating peptides: activatable carriers for targeting systemic delivery of cancer therapeutics and imaging agents," *Wiley Interdiscip Rev Nanomed Nanobiotechnol* 5(1):31-48.

Manuael, E.R. et al. (Jun. 15, 2011, e-published Apr. 28, 2011). "Enhancement of cancer vaccine therapy by systemic delivery of a tumor-targeting *Salmonella*-based STAT3 shRNA suppresses the growth of established melanoma tumor," *Cancer Res* 71(12):4183-4191.

Ohtsuka, E. et al. (Mar. 10, 1985). "An alternative approach to deoxyoligonucleotides as hybridization probes by insertion of deoxyinosine at ambiguous codon positions," *J Biol Chem* 260(5):2605-2608.

Olive, K.P. et al. (Jun. 2009, e-published May 21, 2009). "Inhibition of Hedgehog signaling enhances delivery of chemotherapy in a mouse model of pancreatic cancer," Science 32495933):1457-1461.

Pearson, W.R. et al. (Apr. 1988). "Improved tools for biological sequence comparison," *PNAS USA* 85(8):2444-24448.

Smith, T.F. et al. (1981). "Comparsion of Biosequences," *Adv Appl Math* 2:482-489.

Thompson, C.B.et al. (Nov. 2010, e-published Oct. 26, 2010). "Enzymatic depletion of tumor hyaluronan induces antitumor responses in preclinical animal models," *Mol Cancer Ther* 9(11):3052-3064.

Vermeulen, A. et al. (May 2007, e-published Mar. 30, 2007). "Double-stranded regions are essential design components of potent inhibitors of RISC function," *RNA* 13(5):723-730.

Whatcott, C.J. et al. (Sep. 2011). "Targeting the tumor microenvironment in cancer: why hyaluronidase deserves a second look," *Cancer Discovery* 1(4):291-296.

Written Opinion dated Nov. 6, 2014, for PCT Application No. PCT/US2014/045086, filed Jul. 1, 2014, 7 pages.

Yue, D. et al. (Nov. 2009). "Survey of Computational Algorithms for MicroRNA Target Prediction," *Curr Genomics* 10(7):478-492.

Manuel, E.R. et al. (Sep. 2015, e-published Jul. 1, 2015). "*Salmonella*-Based Therapy Targeting Indoleamine 2,3-Dioxygenase Coupled with Enzymatic Depletion of Tumor Hyaluronan Induces Complete Regression of Aggressive Pancreatic Tumors," *Cancer Immunology Research* 3(9):1096-1107.

Kouji Nagai et al., Ed., "Drug-delivery system no sintenkai" (New Development of Drug Delivery System II)—*Kakusaniyaku koutaiiyaku wakutin iryo wo sasaeru* DDS *gijyutu* (DDS technique that supports nucleic acid medicines, antibody drugs and vaccine treatment), CMC Publishing Co., Ltd, 2012, pp. 225-229. (Partial Translation).

Huang Yuanchun et al. (May 20, 2008). "Role of hyaluronidase in bacterial pathogenesis," *Chinese Journal of Infection and Chemotherapy*, 8(3):235-238.

* cited by examiner

ANTICANCER COMBINATIONS

CROSS-REFERENCE TO RELATED APPLICATION

This application is a continuation of PCT Application No. PCT/US2014/045086, filed Jul. 1, 2014, which claims priority to U.S. Provisional Application No. 61/842,749, filed Jul. 3, 2013, which is incorporated by reference herein in its entirety.

REFERENCE TO A "SEQUENCE LISTING," A TABLE, OR A COMPUTER PROGRAM LISTING APPENDIX SUBMITTED AS AN ASCII FILE

The Sequence Listing written in file 48440532N01US.TXT, created Mar. 14, 2016, 14,609 bytes, machine format IBM-PC, MS-Windows operating system, is hereby incorporated herein by reference in its entirety and for all purposes.

BACKGROUND OF THE INVENTION

Advanced pancreatic ductal adenocarcinoma (PDAC) is often inoperable, and is only transiently responsive to existing therapies. Overexpression of indoleamine 2,3-dioxygenase (IDO) in PDAC plays a major role in accelerating disease progression by suppressing antitumor immunity. Current IDO inhibitors inadequately reverse immunosuppression while systemic off target effects contribute to their toxicity. Thus, there is a need to provide additional cancer therapies that target the immunosuppressive mechanisms associated with tumors and the tumor microenvironment. Provided herein are solutions to these and other problems in the art.

BRIEF SUMMARY OF THE INVENTION

Provided herein are compositions and kits comprising a bacterial cell and a tumor penetrating agent. Also provided are methods of treating cancer in a subject including the step of administering to the subject an effective amount of a bacterial cell and a tumor penetrating agent. Provided are methods of stimulating an immune system in a subject. The methods include administering to the subject an effective amount of a bacterial cell and a tumor penetrating agent. Also provided are methods of enhancing delivery of an anti-cancer agent to a tumor cell including the step of contacting the tumor cell with a bacterial cell, a tumor penetrating agent and an anti-cancer agent.

BRIEF DESCRIPTION OF THE DRAWINGS

FIG. 11 shows that elimination of PDAC tumors using shIDO-ST and PEGPH20™ combination therapy did not result in weight loss.

DETAILED DESCRIPTION OF THE INVENTION

Figure 1:
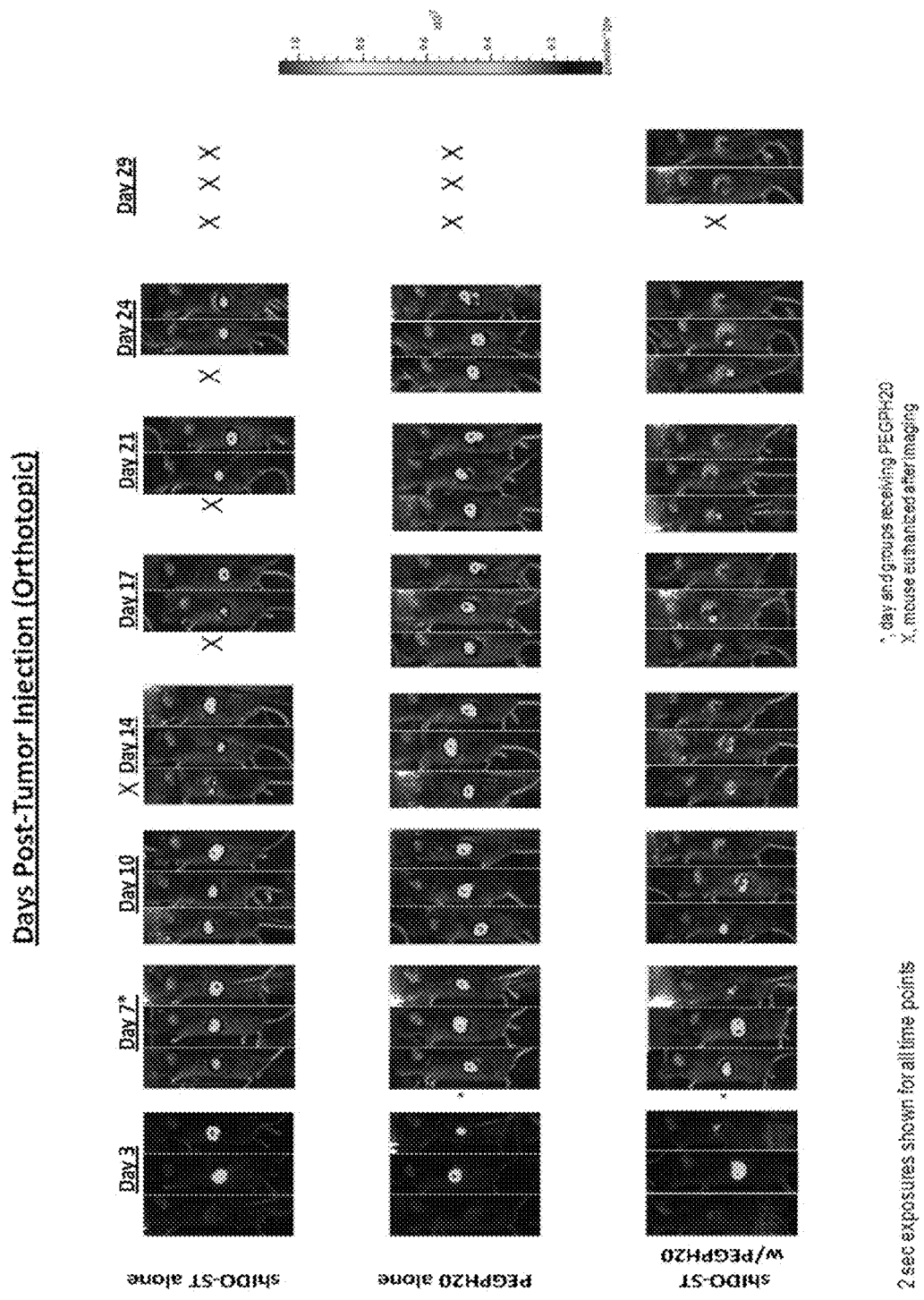
FIG. 1 shows a series of images demonstrating the effects of shIDO-ST, PEGPH20™, and the combination of shIDO-ST and PEGPH20™ in orthotopic KPC-luc model mice. Mice were imaged using an intravital imaging system (IVIS) at the indicated time points after tumor implantation. Tumor reduction was observed with the combined treatment of shIDO-ST and PEGPH20™.

Provided herein are compositions and kits comprising a bacterial cell and a tumor penetrating agent. Also provided are methods of treating cancer in a subject including the step of administering to the subject an effective amount of a bacterial cell and a tumor penetrating agent, wherein administration treats the cancer in the subject.

Provided are methods of stimulating an immune system in a subject. The methods include administering to the subject an effective amount of a bacterial cell and a tumor penetrating agent, wherein administration stimulates the immune system in the subject. Also provided are methods of enhancing delivery of an anti-cancer agent to a tumor cell including the step of contacting the tumor cell with a bacterial cell, a tumor penetrating agent and an anti-cancer agent, wherein contacting the tumor cell with the bacterial cell and tumor penetrating agent enhances delivery of the anti-cancer agent to the tumor cell.

As used herein, the term "tumor penetrating agent" refers to an agent that is capable of penetrating a tumor and/or a tumor cell. Thus, a tumor penetrating agent can penetrate a tumor cell itself or penetrates the area surrounding tumor cells, e.g., the extracellular matrix. By way of example, a tumor penetrating agent penetrates a tumor by breaking down or degrading the extracellular matrix surrounding tumor cells. Alternatively, a tumor penetrating agent penetrates a tumor by entering the tumor cell itself. Examples of tumor penetrating agents for use in the provided compositions and methods include, but are not limited to, hyaluronidase polypeptides, pirfenidone, Saridegib (IPI-926), nanoparticles, albumin nanoparticles, dextrans, liposomes, and cell penetrating peptides. Such tumor penetrating agents including methods of making and using the agents are known and are described in, for example, U.S. Pat. Nos. 7,767,429; 7,829,081; 7,846,431; 7,871,607; 8,105,586; 8,202,517; 8,257,699; 8,431,380; and 8,450,470; Kozono et al., Cancer Res. 73(7):2345-56 (2013); Olive et al., Science 324(5933):1457-61 (2009); Marrache, et al., Curr. Med. Chem. 20(28):3500-14 (2013); Jung, et al., Curr. Med. Chem. 20(28):3488-3499 (2013); Mattheolabakis et al., Nanomedicine (London) 7(10):1577-1590 (2012); Malam, et al., Trends Pharmacol. Sci., 30(11):592-599 (2009); Varshoaz, Expert Opin. Drug Deliv., 9(5):509-23 (2012); MacEwan and Chilkoti, Wiley Interdiscip Rev Nanomed Nanobiotechnol., 5(1):31-48 (2013), which are incorporated by reference herein in their entireties. Optionally, the hyaluronidase polypeptide comprises SEQ ID NO: 1 or SEQ ID NO:2 or a fragment thereof. Optionally, the hyaluronidase polypeptide is a modified hyaluronidase polypeptide. Optionally, the hyaluronidase polypeptide is pegylated. Optionally, the hyaluronidase polypeptide is PEGPH20™ (Halozyme, Inc., San Diego, Calif.).

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., J. Biol. Chem. 273(52):35095-35101 (1998).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins. Software for performing BLAST analyses is publicly available through the National Center for Biotechnology Information, as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89: 10915 (1989)) alignments (B) of 50, expectation (E) of 10, M=5, N=−4, and a comparison of both strands.

An "inhibitory nucleic acid" is a nucleic acid (e.g. DNA, RNA, polymer of nucleotide analogs) that is capable of binding to a target nucleic acid (e.g. an mRNA translatable into PTPRS) and reducing transcription of the target nucleic acid (e.g. mRNA from DNA) or reducing the translation of the target nucleic acid (e.g. mRNA) or altering transcript splicing (e.g. single stranded morpholino oligo) relative to the absence of the inhibitory nucleic acid. A "morpholino oligo" may be alternatively referred to as a "morphlino nucleic acid" and refers to morpholine-containing nucleic acid nucleic acids commonly known in the art (e.g. phosphoramidate morpholino oligo or a "PMO"). See Marcos, P., Biochemical and Biophysical Research Communications 358 (2007) 521-527. In some embodiments, the "inhibitory nucleic acid" is a nucleic acid that is capable of binding (e.g. hybridizing) to a target nucleic acid (e.g. an mRNA translatable into an RPTPS) and reducing translation of the target nucleic acid. The target nucleic acid is or includes one or more target nucleic acid sequences to which the inhibitory nucleic acid binds (e.g. hybridizes). Thus, an inhibitory nucleic acid typically is or includes a sequence (also referred to herein as an "antisense nucleic acid sequence") that is capable of hybridizing to at least a portion of a target nucleic acid at a target nucleic acid sequence. An example of an inhibitory nucleic acid is an antisense nucleic acid. Another example of an inhibitory nucleic acid is siRNA or RNAi (including their derivatives or pre-cursors, such as nucleotide analogs). Further examples include shRNA, miRNA, shmiRNA, or certain of their derivatives or pre-cursors. In some embodiments, the inhibitory nucleic acid is single stranded. In other embodiments, the inhibitory nucleic acid is double stranded.

An "antisense nucleic acid" is a nucleic acid (e.g. DNA, RNA or analogs thereof) that is at least partially complementary to at least a portion of a specific target nucleic acid (e.g. a target nucleic acid sequence), such as an mRNA molecule (e.g. a target mRNA molecule) (see, e.g., Weintraub, Scientific American, 262:40 (1990)), for example antisense, siRNA, shRNA, shmiRNA, miRNA (microRNA). Thus, antisense nucleic acids are capable of hybridizing to (e.g. selectively hybridizing to) a target nucleic acid (e.g. target mRNA). In some embodiments, the antisense nucleic acid hybridizes to the target nucleic acid sequence (e.g. mRNA) under stringent hybridization conditions. In some embodiments, the antisense nucleic acid hybridizes to the target nucleic acid (e.g. mRNA) under moderately stringent hybridization conditions. Antisense nucleic acids may comprise naturally occurring nucleotides or modified nucleotides such as, e.g., phosphorothioate, methylphosphonate, and -anomeric sugar-phosphate, backbonemodified nucleotides. An "anti-PTPRS antisense nucleic acid" is an antisense nucleic acid that is at least partially complementary to at least a portion of a target nucleic acid sequence, such as an mRNA molecule, that codes at least a portion of the PTPRS. In some embodiments, an antisense nucleic acid is a morpholino oligo. In some embodiments, a morpholino oligo is a single stranded antisense nucleic acid, as is known in the art. In some embodiments, a morpholino oligo decreases protein expression of a target, reduces translation of the target mRNA, reduces translation initiation of the target mRNA, or modifies transcript splicing. In some embodiments, the morpholino oligo is conjugated to a cell permeable moiety (e.g. peptide). Antisense nucleic acids may be single or double stranded nucleic acids.

In the cell, the antisense nucleic acids may hybridize to the target mRNA, forming a double-stranded molecule. The antisense nucleic acids, interfere with the translation of the mRNA, since the cell will not translate a mRNA that is double-stranded. The use of antisense methods to inhibit the in vitro translation of genes is well known in the art (Marcus-Sakura, Anal. Biochem., 172:289, (1988)). Antisense molecules which bind directly to the DNA may be used.

Inhibitory nucleic acids can be delivered to the subject using any appropriate means known in the art, including by injection, inhalation, or oral ingestion. Another suitable delivery system is a colloidal dispersion system such as, for example, macromolecule complexes, nanocapsules, microspheres, beads, and lipid-based systems including oil-in-water emulsions, micelles, mixed micelles, and liposomes. An example of a colloidal system of this invention is a liposome. Liposomes are artificial membrane vesicles which are useful as delivery vehicles in vitro and in vivo. Nucleic acids, including RNA and DNA within liposomes and be delivered to cells in a biologically active form (Fraley, et al., Trends Biochem. Sci., 6:77, 1981). Liposomes can be targeted to specific cell types or tissues using any means known in the art. Inhibitory nucleic acids (e.g. antisense nucleic acids, morpholino oligos) may be delivered to a cell using cell permeable delivery systems (e.g. cell permeable peptides). In some embodiments, inhibitory nucleic acids are delivered to specific cells or tissues using viral vectors or viruses.

An "siRNA" refers to a nucleic acid that forms a double stranded RNA, which double stranded RNA has the ability to reduce or inhibit expression of a gene or target gene when the siRNA is present (e.g. expressed) in the same cell as the gene or target gene. The siRNA is typically about 5 to about 100 nucleotides in length, more typically about 10 to about 50 nucleotides in length, more typically about 15 to about 30 nucleotides in length, most typically about 20-30 base nucleotides, or about 20-25 or about 24-29 nucleotides in length, e.g., 20, 21, 22, 23, 24, 25, 26, 27, 28, 29, or 30 nucleotides in length. siRNA molecules and methods of generating them are described in, e.g., Bass, 2001, Nature, 411, 428-429; Elbashir et al., 2001, Nature, 411, 494-498; WO 00/44895; WO 01/36646; WO 99/32619; WO 00/01846; WO 01/29058; WO 99/07409; and WO 00/44914. A DNA molecule that transcribes dsRNA or siRNA (for instance, as a hairpin duplex) also provides RNAi. DNA molecules for transcribing dsRNA are disclosed in U.S. Pat. No. 6,573,099, and in U.S. Patent Application Publication Nos. 2002/0160393 and 2003/0027783, and Tuschl and Borkhardt, Molecular Interventions, 2:158 (2002). Small or short hairpin RNA molecules (shRNA) are generated by such DNA molecules, e.g., within cells by transcription. ShRNAs typically include two complementary RNA sequences linked by a short loop of nucleotides similar to the hairpin found in naturally occurring miRNA. Typically, shRNA molecules are about 20-30 base nucleotides, or about 19-22, or about 20-25 or about 24-29 nucleotides in length, e.g., 20, 21, 22, 23, 24, 25, 26, 27, 28, 29, or 30 nucleotides in length, with the short loop of nucleotides forming the hairpin being about 4, 5, 6, 7, 8, 9, 10, 11, or 12 nucleotides in length.

The siRNA can be administered directly or siRNA expression vectors can be used to induce RNAi that have different design criteria. A vector can have inserted two inverted repeats separated by a short spacer sequence and ending with a string of T's which serve to terminate transcription.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al., John Wiley & Sons.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C. to 95° C. for 30 seconds to 2 minutes, an annealing phase lasting 30 seconds to 2 minutes, and an extension phase of about 72° C. for 1 to 2 minutes. Protocols and guidelines for low and high stringency amplification reactions are provided, e.g., in Innis et al. (1990) PCR Protocols, A Guide to Methods and Applications, Academic Press, Inc. N.Y.).

A "control" sample or value refers to a sample that serves as a reference, usually a known reference, for comparison to a test sample. For example, a test sample can be taken from a test condition, e.g., in the presence of a test agent, and compared to samples from known conditions, e.g., in the absence of the test agent (negative control), or in the presence of a known agent (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and Medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulinoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The P388 leukemia model is widely accepted as being predictive of in vivo anti-leukemic activity. It is believed that a compound that tests positive in the P388 assay will generally exhibit some level of anti-leukemic activity in vivo regardless of the type of leukemia being treated. Accordingly, the present application includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

ShIDO-ST is a *Salmonella typhimurium* (ST) cell that expresses a small hairpin (sh)RNA to specifically silence indoleamine-pyrrole 2,3-dioxygenase (IDO) with decreased toxicity. Specifically, shIDO-ST is composed of an attenuated *Salmonella typhimurium* strain known as YS1646 (ATCC Accession No. 202165, also referred to herein as VNP20009) expressing a small hairpin RNA targeted to IDO comprising SEQ ID NO:8. This cell based therapy has been described in, for example, WO2012/149364, which is incorporated by reference herein in its entirety. As described in the examples below, the combination of pegylated recombinant human hyaluronidase PH20 (PEGPH20™, Halozyme Inc., San Diego, Calif.), which depletes hyaluronan abundant in tissue and increases vascular permeability, and shIDO-ST resulted in effective control of and, in some cases, complete elimination of established pancreatic tumors in autochthonous and orthotopic models. Further, it was observed that ST containing a control small hairpin RNA in combination with PEGPH20™ was also able to control tumor growth when tumors were of smaller size. Recombinant human hyaluronidase PH20 and the pegylated form of PH20 are known and described in, for example, Bookbinder et al., Journal of Controlled Release, 114:230-241 (2006) and Thompson et al., Mol. Cancer Ther. 9:3052-3064 (2010), which are incorporated by reference herein in their entireties.

Thus, provided are compositions comprising a bacterial cell and a tumor penetrating agent. Optionally, the composition further comprises an anti-cancer agent. The anti-cancer agent can be selected from the group consisting of a small molecule, a nucleic acid, a polypeptide and an antibody. Examples of tumor penetrating agents include, but are not limited to, hyaluronidase polypeptides, pirfenidone, Saridegib (IPI-926), nanoparticles, albumin nanoparticles, dextrans, liposomes, and cell penetrating peptides. In certain embodiments, the tumor penetrating agent is a hyaluronidase polypeptide. Optionally, the bacterial cell and hyaluronidase polypeptide are present in an effective amount, e.g., a synergistic effective amount. Optionally, the bacterial cell is a *Salmonella* bacterial cell. Thus, provided are compositions comprising a *Salmonella* bacterial cell and a hyaluronidase polypeptide.

Hyaluronidases are a group of neutral- and acid-active enzymes generally grouped in three different classes, mammalian-type hyaluronidases, bacterial hyaluronidases and hyaluronidases from leeches, other parasites and crustaceans. Mammalian-type hyaluronidases are endo-beta-N-acetylhexosaminidases that have both hydrolytic and transglycosidase activities, and can be further divided into two groups, neutral active and acid active enzymes. There are six hyaluronidase-like genes in the human genome, HYAL1, HYAL2, HYAL3 HYAL4 HYALP1 and PH20/SPAM1, which can degrade hyaluronan and chondroitin sulfates (CS), specifically C4-S and C6-S. Hyaluronan is found in the extracellular matrix of many cells and plays a key role in biological phenomena associated with cell mobility including tumorigenesis. Hyaluronidase polypeptides suitable for use in the provided methods and compositions include mammalian hyaluronidases, for example, PH-20 hyaluronidase. Optionally, the hyaluronidase polypeptide comprises SEQ ID NO: 1 or SEQ ID NO:2 or a fragment thereof. As used throughout, the term "hyaluronidase polypeptide" includes domains, fragments, and variants thereof. Thus, as described herein, the hyaluronidase polypeptide can comprise a fragment of SEQ ID NO: 1 or SEQ ID NO:2 as long as the fragment remains catalytically active, e.g., the polypeptide retains the ability to degrade hyaluron and/or chondroitin sulfate. Further, the hyaluronidase polypeptide can comprise SEQ ID NO:1 or SEQ ID NO:2 or a fragment of SEQ ID NO: 1 or SEQ ID NO:2 with one or more amino acid substitutions again as long as the hyaluronidase polypeptide remains catalytically active. Optionally, the amino acid substitution is a conservative amino acid substitution as described in more detail above. By way of an example, the hyaluronidase polypeptide can include a fragment of SEQ ID NO: 1, e.g., amino acids 35-464 of SEQ ID NO:1 or the entire sequence of amino acids set forth in SEQ ID NO:1. Exemplary nucleic acid sequences of hyaluronidases can be found, for example, at GenBank Accession Nos. NM_003117 and NM_153189.2 and exemplary polypeptide sequences of hyaluronidases can be found, for example, at GenBank Accession Nos. NP_003108 and NP_694859. Hyaluronidase polypeptides suitable for use in the provided compositions, kits and methods are described in U.S. Pat. Nos. 7,767,429; 7,829,081; 7,846,431; 7,871,607; 8,105, 586; 8,202,517; 8,257,699; 8,431,380; and 8,450,470, each of which are incorporated by reference herein in their entirety. Optionally, the hyaluronidase polypeptide is a chemically modified hyaluronidase polypeptide, i.e., the polypeptide has been modified to include one or more glycosylated and/or pegylated moieties. Optionally, the hyaluronidase polypeptide is pegylated. Optionally, the hyaluronidase polypeptide is PEGPH20™ (Halozyme, Inc., San Diego, Calif.), which is used in the examples below. PEGPH20™ (Halozyme, Inc., San Diego, Calif.), is recombinant human hyaluronidase PH-20 (SEQ ID NO: 1) that has been modified by pegylation. Thus, PEGPH20™ (Halozyme, Inc., San Diego, Calif.), is pegylated recombinant human hyaluronidase PH-20.

As used herein, the terms peptide, polypeptide, or protein are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more. It is understood that the nucleic acids that can encode those peptide, polypeptide, or protein sequences, variants and fragments thereof are also disclosed. This would include all degenerate sequences related to a specific polypeptide sequence, i.e. all nucleic acids having a sequence that encodes one particular polypeptide sequence as well as all nucleic acids, including degenerate nucleic acids, encoding the disclosed variants and derivatives of the polypeptide sequences. Thus, while each particular nucleic acid sequence may not be written out herein, it is understood that each and every sequence is in fact disclosed and described herein through the disclosed polypeptide sequence.

As with all peptides, polypeptides, and proteins, including fragments thereof, it is understood that additional modifications in the amino acid sequence of the provided agents that are polypeptides can occur that do not alter the nature or function of the peptides, polypeptides, or proteins. Thus, modification of the hyaluronidase polypeptide can be made as long as the hyaluronidase polypeptide remains catalytically active, e.g., the polypeptide retains the ability to degrade hyaluron and/or chondroitin sulfate. Such modifications include, for example, conservative amino acids substitutions. Thus, the provided agents comprising polypeptides or nucleic acids can be further modified and varied so long as the desired function is maintained. It is understood that one way to define any known modifications and derivatives or those that might arise, of the disclosed nucleic acid sequences and proteins herein is through defining the modifications and derivatives in terms of identity to specific known sequences. Specifically disclosed are polypeptides which have at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the polypeptides provided herein. Those of skill in the art readily understand how to determine the identity of two polypeptides as discussed in more detail above.

Bacterial cells useful in the provided composition, kits and methods include, but are not limited to *Salmonella* bacterial cells, Bifidobacteria bacterial cells, *Listeria monocytogenes* bacterial cells, *Clostridium histolyticus* bacterial cells, *Clostridium novyi* bacterial cells, *Vibrio cholera* bacterial cells, *Shigella* bacterial cells, *Streptococcus* bacterial cells, *Mycobacterium bovis* bacterial cells, *Yersinia enterocolitica* bacterial cells, *Bacillus anthracis* bacterial cells, Lactobacillus bacterial cells, Staphylococcus bacterial cells, E. coli bacterial cells. Optionally, the Streptococcus bacterial cells are Streptococcus pyrogenes bacterial cells or Streptococcus gordonii bacterial cells. Suitable bacterial cells include bacterial cells described in International Publication No. WO 2012/149364, which is incorporated by reference herein in its entirety. Optionally, the Salmonella bacterial cell is an attenuated Salmonella strain, for example, any serovar or Salmonella enterica, including, but not limited to, Salmonella typhimurium, Salmonella enteritidis or Salmonella typhi. Optionally, the Salmonella bacterial cell is an attenuated strain of Salmonella typhimurium. Attenuated Salmonella typhimurium strains include, but are not limited to, YS1646, RE88, LH430, SL7207, χ8429, χ8431 or χ8468. Optionally, the attenuated Salmonella typhimurium strain is a YS1646 Salmonella typhimurium strain (ATCC Accession No. 202165, also referred to herein as VNP20009), which is the strain used in the examples below and used to generate shIDO-ST.

Optionally, the bacterial cells provided herein comprise one or more molecules suitable for the treatment of a disease or disorder. Optionally, the disease or disorder is cancer. Thus, the bacterial cell can comprise one or more agents capable of blocking, inhibiting or suppressing target gene expression or a target protein activity including, but not limited to, antibodies or functional fragments thereof, small molecules, aptamers, nucleic acids and RNA interference molecules (e.g., small interfering RNA (siRNA), microRNA (miRNA) and small hairpin RNA (shRNA)). Optionally, the bacterial cell comprises a functional nucleic acid, e.g., an antisense nucleic acid.

Functional nucleic acids are nucleic acid molecules that have a specific function, such as binding a target molecule or catalyzing a specific reaction. Functional nucleic acid molecules can interact with any macromolecule, such as DNA, RNA, polypeptides, or carbohydrate chains. Thus, functional nucleic acids can interact with a target molecule directly. Often functional nucleic acids are designed to interact with other nucleic acids based on sequence homology between the target molecule and the functional nucleic acid molecule.

Antisense nucleic acids or antisense oligonucleotides (ASOs) are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. See for example, Vermeulen et al., RNA 13: 723-730 (2007) and in WO2007/095387 and WO 2008/036825; Yue, et al., Curr. Genomics, 10(7):478-92 (2009) and Lennox Gene Ther. 18(12):1111-20 (2011), which are incorporated by reference herein in their entireties. Optionally, the antisense nucleic acid is a short hairpin RNA, which is a sequence of RNA that makes a tight hairpin turn. Optionally, the antisense nucleic acid is an siRNA or an miRNA. Antisense nucleic acid can be designed and made using standard nucleic acid synthesis techniques or obtained from a commercial entity, e.g., Sigma-Aldrich (St. Louis, Mo.) or Regulus Therapeutics (San Diego, Calif.).

Optionally, the backbone of the antisense nucleic acid is modified by various chemical modifications to improve the in vitro and in vivo stability and to improve the in vivo delivery of antisense molecules. Modifications of antisense molecules include, but are not limited to, 2'-O-methyl modifications, 2'-O-methyl modified ribose sugars with terminal phosphorothioates and a cholesterol group at the 3' end, 2'-O-methoxyethyl (2'-MOE) modifications, 2'-fluoro modifications, and 2',4' methylene modifications (referred to as "locked nucleic acids" or LNAs). Thus, inhibitory nucleic acids include, for example, modified oligonucleotides (2'-O-methylated or 2'-O-methoxyethyl), locked nucleic acids (LNA; see, e.g, Valóczi et al., Nucleic Acids Res. 32(22): e175 (2004)), morpholino oligonucleotides (see, e.g, Kloosterman et al., PLoS Biol 5 (8): e203 (2007)), peptide nucleic acids (PNAs), PNA-peptide conjugates, and LNA/2'-O-methylated oligonucleotide mixmers (see, e.g., Fabiani and Gait, RNA 14:336-46 (2008)).

Optionally, the antisense nucleic acid targets a metabolic enzyme, an immunosuppressive target or a cancer target. Optionally, the antisense nucleic acid targets an immunosuppressive target and the immunosuppressive target is STAT3, IDO1, IDO2, Arginase 1, iNOS, CTLA-4, TGF-β, IL-10, pGE2 or VEGF. Optionally, the immunosuppressive target is IDO1.

Suppression, inhibition or blockade of the immunosuppressive target gene or protein ultimately results in disruption of tumor-derived immunosuppression within the tumor microenvironment through direct or indirect mechanisms. Thus, the agent may be an antisense nucleic acid that targets STAT3, IDO1, IDO2, Arginase 1 (Arg1), iNOS, CTLA-4, IL-10, VEGF, pEGF2, or TGF-β. These targets including their amino acid and nucleic acid sequences are known and, as is known and described herein, the nucleic acid sequences of these targets can be used to generate inhibitory nucleic acid molecules including antisense oligonucleotides and short hairpin RNA using known methods. By way of example, the bacterial cells can comprise one or more of any of the following antisense nucleic acids of SEQ ID NOs: 3-31. Thus, the antisense nucleic acid can target STAT3 and can be short hairpin RNA comprising shSTAT3 #58: AGTTCCTGGCACCTTGGATTGAGAGTCAA (SEQ ID NO:3), shSTAT3 #59: ACTGGATAACTTCATT-AGCAGAATCTCAA (SEQ ID NO:4), shSTAT3 #60: CAT-CAATCCTGTGGTATAACATGCTGACC (SEQ ID NO:5), or shSTAT3 #61: ACCTGAAGACCAAGTT-CATCTGTGTGACA (SEQ ID NO:6). The antisense nucleic acid can target IDO1 and can be short hairpin RNA comprising shIDO1-8: CCTCGCAATAGTAGATACT (SEQ ID NO:7), shIDO1-9: CGTCTCTCTATTGGTGAA. (SEQ ID NO:8), shIDO1-10: GCAAAGAATCTCCTGCAGA (SEQ ID NO:9), shIDO1-11: GCCCATGACATACGAGAAC (SEQ ID NO:10), or shIDO1-12: CCAGTCCGT-GAGTTTGTCA (SEQ ID NO: 11). The antisense nucleic acid can target Arg1 and can be short hairpin RNA comprising shArg1-5: GCAGTTCCTTTCTGGTATG (SEQ ID NO:12), shArg1-6: GCCTTTGTTGATGTCCCT (SEQ ID NO:13), shArg1-7: CCAGGGACTGACTACCTTA (SEQ ID NO: 14), shArg1-8: GCCAAAGACATCGTGTACA (SEQ ID NO:15), or shArg1-9: TCTCTACAT-CACAGAAGA (SEQ ID NO:16). The antisense nucleic acid can target iNOS and can be short hairpin RNA comprising shiNOS-43: GTATTGTACTATTGTGGACTA (SEQ ID NO:17), shiNOS-44: CCAGTATTATGGCTCCTTTAA (SEQ ID NO:18), shiNOS-45: GCCACAGCAATATAGGCTCAT (SEQ ID NO: 19), shiNOS-46: CCTATCTCCATTCTACTACTA (SEQ ID NO:20), or shiNOS-47: GCTGTAACAAAGGAAATAGAA (SEQ ID NO:21). The antisense nucleic acid can target IDO2 and can be short hairpin RNA comprising CGCAGTTATGAGCTTTCTTAA (SEQ ID NO:22), CCGCAGTTATGAGCTTTCTTA (SEQ ID NO:23), CCTGGGATAAAGGCTCTTGTT (SEQ ID NO:24), GAAAGCTATCACATATCTGAA (SEQ ID NO:25), CTTTGGAAAGCTATCACATAT (SEQ ID NO:26), CCATTGTCTTTGGAAAGCTAT (SEQ ID NO:27), CTTCTTCCAGATTCTCTGAAA (SEQ ID NO:28), GCTTCAAGCTCATGTGGACAA (SEQ ID NO:29), CAAGGAATCTTGCCCTTCCAT (SEQ ID NO:30), GCAGTGCCATTGTCTTTGGAA (SEQ ID NO:31). As discussed above, antisense molecules can be readily designed and obtained using the nucleic acid sequence of a known target using known methods. For example, antisense molecules can be designed and made using standard nucleic acid synthesis techniques or obtained from a commercial entity, e.g., Regulus Therapeutics (San Diego, Calif.).

The agents capable of blocking, inhibiting or suppressing target gene expression or a target protein activity, e.g., antisense nucleic acids, can be expressed from an expression vector or cassette in the bacterial cell. Suitable expression vectors, e.g., plasmids, and their methods of use are known.

Provided herein are compositions including the agents provided herein. Provided compositions can include a single agent, e.g., a bacterial cell or more than one agent, e.g., a bacterial cell and tumor penetrating agent. The provided compositions are, optionally, suitable for formulation and administration in vitro or in vivo. Optionally, the compositions comprise one or more of the provided agents and a pharmaceutically acceptable carrier. Suitable carriers and their formulations are described in Remington: *The Science and Practice of Pharmacy*, 21st Edition, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

The term "pharmaceutically acceptable salts" or "pharmaceutically acceptable carrier" is meant to include salts of the active agents which are prepared with relatively nontoxic acids or bases, depending on the particular substituents found on the agents described herein. When agents of the present application contain relatively acidic functionalities, base addition salts can be obtained by contacting the neutral form of such agents with a sufficient amount of the desired base, either neat or in a suitable inert solvent. Examples of pharmaceutically acceptable base addition salts include sodium, potassium, calcium, ammonium, organic amino, or magnesium salt, or a similar salt. When agents of the present application contain relatively basic functionalities, acid addition salts can be obtained by contacting the neutral form of such agents with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Other pharmaceutically acceptable carriers known to those of skill in the art are suitable for compositions of the present application.

The agents are administered in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, intracavity, transdermal, oral, topical, intratumoral, parenteral, or inhalation routes. Thus, the compositions are administered in a number of ways depending on whether local or systemic treatment is desired, and on the area to be treated.

The compositions for administration will commonly comprise an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Solutions of the active agents as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active agents may be incorporated with excipients and used in the form of ingestible tablets, buccal tablets, troches, capsules, elixirs, suspensions, syrups, wafers, and the like. Such compositions and preparations should contain at least 0.1% of active agent. The percentage of the compositions and preparations may, of course, be varied and may conveniently be between about 2 to about 75% of the weight of the unit, or preferably between 25-60%. The amount of active agents in such compositions is such that a suitable dosage can be obtained For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion Sterile injectable solutions can be prepared by incorporating the active agents or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of agents can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

The compositions and agents as described herein are useful for both prophylactic and therapeutic treatment. For prophylactic use, a therapeutically effective amount of the agents described herein are administered to a subject prior to or during early onset (e.g., upon initial signs and symptoms of cancer). Therapeutic treatment involves administering to a subject a therapeutically effective amount of the agents described herein after diagnosis or development of disease.

Provided herein is a method of treating cancer in a subject comprising administering to the subject an effective amount, e.g., a combined effective amount, of a bacterial cell and a tumor penetrating agent, wherein administration treats the cancer in the subject. Optionally, the effective amount or combined effective amount is a synergistic amount or combined synergistic effective amount. Also provided is a method of stimulating an immune system in a subject comprising administering to the subject an effective amount of a bacterial cell and a tumor penetrating agent, wherein administration of the bacterial cell and the tumor penetrating agent stimulates the immune system of the subject. Optionally, the immune response is an anti-cancer immune response. Optionally, the provided methods further include administering to the subject an anti-cancer agent. Optionally, the anti-cancer agent is administered subsequent to administration of the bacterial cell and tumor penetrating agent.

Further provided is a method of enhancing delivery of an anti-cancer agent to a tumor cell comprising contacting the tumor cell with a bacterial cell, a tumor penetrating agent and an anti-cancer agent, wherein administration of the bacterial cell and cell penetrating agent enhances delivery of the anti-cancer agent.

Anti-cancer agent can be selected from the group consisting of a small molecule, a nucleic acid, a polypeptide, and an antibody. Anti-cancer agents are known to those of skill in the art. See, e.g., *Physician's Drug Handbook*, 12th Edition, Lippincott, Williams & Wilkins, (2007) or *Physician's Cancer Chemotherapy Drug Manual* 2013, by Chu and DeVita, Jones & Bartlett Learning, LLC, (2013). Optionally, the anti-cancer agent is a chemotherapeutic agent. Chemotherapeutic agents are agents which may inhibit the growth of tumors. Such agents, include, but are not limited to 5-fluorouracil; gemcitabine; mitomycin C; methotrexate; hydroxyurea; cyclophosphamide; dacarbazine; mitoxantrone; anthracyclins (epirubicin and doxurubicin); antibodies to receptors, such as herceptin; etoposide; pregnasome; hormone therapies such as tamoxifen and anti-estrogens; interferons; aromatase inhibitors; progestational agents; and LHRH analogs.

Optionally, in the provided methods the tumor penetrating agent is administered prior to the bacterial cell. When the methods include administration of an anti-cancer agent, the anti-cancer agent can be administered after administration of the bacterial cell and/or tumor penetrating agent. Thus, combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions.

In the provided methods, the bacterial cell and hyaluronidase polypeptide are, optionally, present in an effective amount, e.g., a synergistic effective amount. Optionally, the bacterial cell is a *Salmonella* bacterial cell. Optionally, the tumor penetrating agent is a hyaluronidase polypeptide. Optionally, the hyaluronidase polypeptide comprises SEQ ID NO: 1 or SEQ ID NO:2 or a fragment thereof. Hyaluronidase polypeptides suitable for use in the provided compositions, kits and methods are described in U.S. Pat. Nos. 7,767,429; 7,829,081; 7,846,431; 7,871,607; 8,105,586; 8,202,517; 8,257,699; 8,431,380; and 8,450,470, each of which are incorporated by reference herein in their entirety. Optionally, the hyaluronidase polypeptide is a modified hyaluronidase polypeptide. Optionally, the hyaluronidase polypeptide is pegylated. Optionally, the hyaluronidase polypeptide is PEGPH20™ (Halozyme, Inc., San Diego, Calif.).

Optionally, the tumor penetrating agent is selected from the group consisting of pirfenidone (Kozono et al., Cancer Res. 73(7):2345-56 (2013)), IPI-929 (Olive et al., Science 324(5933):1457-61 (2009)), nanoparticles, albumin nanoparticles, dextrans, liposomes, and cell penetrating peptides.

Bacterial cells useful in the provided methods include, but are not limited to, *Salmonella* bacterial cells, Bifidobacteria bacterial cells, *Listeria monocytogenes* bacterial cells, *Clostridium histolyticus* bacterial cells, *Clostridium novyi* bacterial cells, *Vibrio cholera* bacterial cells, *Shigella* bacterial cells, *Streptococcus* bacterial cells, *Mycobacterium bovis* bacterial cells, *Yersinia enterocolitica* bacterial cells, *Bacillus anthracis* bacterial cells, *Lactobacillus* bacterial cells, *Staphylococcus* bacterial cells, *E. coli* bacterial cells. Optionally, the *Streptococcus* bacterial cells are *Streptococcus pyrogenes* bacterial cells or *Streptococcus gordonii* bacterial cells. Suitable bacterial cells include bacterial cells described in International Publication No. WO 2012/149364, which is incorporated by reference herein in its entirety. Optionally, the *Salmonella* bacterial cell is an attenuated *Salmonella* strain. Optionally, the *Salmonella* bacterial cell is a *Salmonella choleraesuis* bacterial cells. Optionally, the *Salmonella* bacterial cell is an attenuated strain of *Salmonella typhimurium*. Attenuated *Salmonella typhimurium* strains include, but are not limited to, YS1646, RE88, LH430, SL7207, χ8429, χ8431 or χ8468. Optionally, the attenuated *Salmonella typhimurium* strain is an YS1646 *Salmonella typhimurium* strain (ATCC Accession No. 202165, also referred to herein as VNP20009). Optionally, *Toxoplasma gondii* cells can be used in the provided compositions, kits and methods.

Optionally, the bacterial cells provided herein comprise one or more molecules suitable for the treatment of a disease or disorder. Thus, the bacterial cell can comprise one or more agents capable of blocking, inhibiting or suppressing target gene expression or a target protein activity including, but not limited to, antibodies or functional fragments thereof, small molecules, aptamers, nucleic acids and RNA interference molecules (e.g., small interfering RNA (siRNA), microRNA (miRNA) and small hairpin RNA (shRNA)). Optionally, the bacterial cell comprises a functional nucleic acid, e.g., an antisense nucleic acid. Optionally, the antisense nucleic acid targets a metabolic enzyme, an immunosuppressive target or a cancer target. Optionally, the antisense nucleic acid targets an immunosuppressive target and the immunosuppressive target is STAT3, IDO1, IDO2, Arginase 1, iNOS, CTLA-4, TGF-β, IL-10, pGE2 or VEGF. Optionally, the immunosuppressive target is IDO1. Optionally, the antisense nucleic acid is selected from the group consisting of SEQ ID NOs:3-31.

By "effective dose or amount" herein is meant a dose that produces effects for which it is administered. By "combined effective dose or amount" herein is meant a dose of two or more agents administered concomitantly (e.g., as a mixture), separately but simultaneously (e.g., via separate intravenous lines) or sequentially (e.g., one agent is administered first followed by administration of the second agent), that produces effects for which it is administered. For example, therapeutically effective amount or combined effect amount includes that amount of an agent or combination of agents sufficient to reduce or ameliorate one or more symptoms of a disease or disorder. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)).

The terms "synergistic," "synergistic effect," "synergistic therapeutic effect," "synergistically effective amount" and the like in the context of co-administration of agents described herein refer to a more than additive (e.g., supra-additive) response (e.g., biological response) when two or more agents are administered with respect to the summed effects upon administration of each agent in the absence of the other agent or agents. For example, if two agents provide a synergistic therapeutic effect, then the therapeutic effect observed upon co-administration of both agents is greater than the summed observed therapeutic effects when either agent is administered in the absence of the other agent. Likewise, a first amount of a first agent and a second amount of a second agent together provide a synergistically effective amount where the therapeutic effect observed upon co-administration of both agents is greater than the summed observed therapeutic effects when either agent is administered in the absence of the other agent.

As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

A "subject," "individual," or "patient," is used interchangeably herein, which refers to a vertebrate, preferably a mammal, more preferably a human. Mammals include, but are not limited to, murines, simians, humans, farm animals, sport animals, and pets. Tissues, cells and their progeny of a biological entity obtained in vitro or cultured in vitro are also encompassed.

Provided herein are kits comprising one or more of the provided compositions. Thus, provided are kits comprising a bacterial cell and a tumor penetrating agent. Optionally, the bacterial cell and tumor penetrating agent are present in an effective amount, e.g., a synergistic effective amount. Optionally, the kits comprise a first composition comprising a *Salmonella* bacterial cell and a second composition comprising a hyaluronidase polypeptide. Optionally, the *Salmonella* bacterial cell and hyaluronidase polypeptide are present in an effective amount, e.g., a synergistic effective amount. Optionally, the compositions are present in a container such as a vial or packet. Optionally, the kit comprises one or more additional agents. Thus, for example, the kit further includes an additional therapeutic agent, e.g., an anti-cancer agent. The additional therapeutic agent may be included in a composition comprising the bacterial cell and/or tumor penetrating agent or formulated as a separate composition. Optionally, the kit comprises a means of administering the compositions, such as, for example, a syringe, needle, tubing, catheter, patch, and the like. The kit may also comprise formulations and/or materials requiring sterilization and/or dilution prior to use. Optionally, the provided kits include instructions for use.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these agents may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

A number of embodiments have been described. Nevertheless, it will be understood that various modifications may be made. Accordingly, other embodiments are within the scope of the claims.

EXAMPLE

Example 1

Combination of shIDO-ST and PEGPH20™ for Cancer Treatment

To determine the effects of shIDO-ST and PEGPH20™, nine C57BL/6 mice were injected orthotopically (in the pancreas) with $5\times10^5$ KPC-luc cells. Three small groups (n=3) were created: shIDO-ST alone, PEGPH20™ alone, and shIDO-ST with PEGPH20™. The shIDO-ST alone group received shIDO-ST at a dose of $5\times10^6$ cfu/mouse through intravenous (i.v.) injection on days 8 and 12. PEGPH20™ alone group received PEGPH20™ at a dose of 4.5 mg/kg (~90 ug/mouse) on day 7 through i.v. injection. The combination (PEGPH20™ with shIDO-ST) group received PEGPH20™ at 4.5 mg/kg on day 7 followed by treatment with shIDO-ST on day 8 at $5\times10^6$ cfu/mouse. Mice were imaged using an intravital imaging system (IVIS) at indicated time points after tumor cell implantation. Mice were injected with D-luciferin at indicated days and imaged 5-10 minutes post-injection. Exposure time was 2 seconds for all time points. In both the shIDO-ST group and combination group, mice exhibited signs of sickness due to toxicity of the shIDO-ST, which was likely a result of too high a dose. Tumor reduction in the combination group, and to a lesser degree in the shIDO-ST alone group, was observed. Mice in the PEGPH20™ group were euthanized due to significantly large tumors which caused problems with mobility in all cases and sickness in two of the three mice.

Figure 2A:
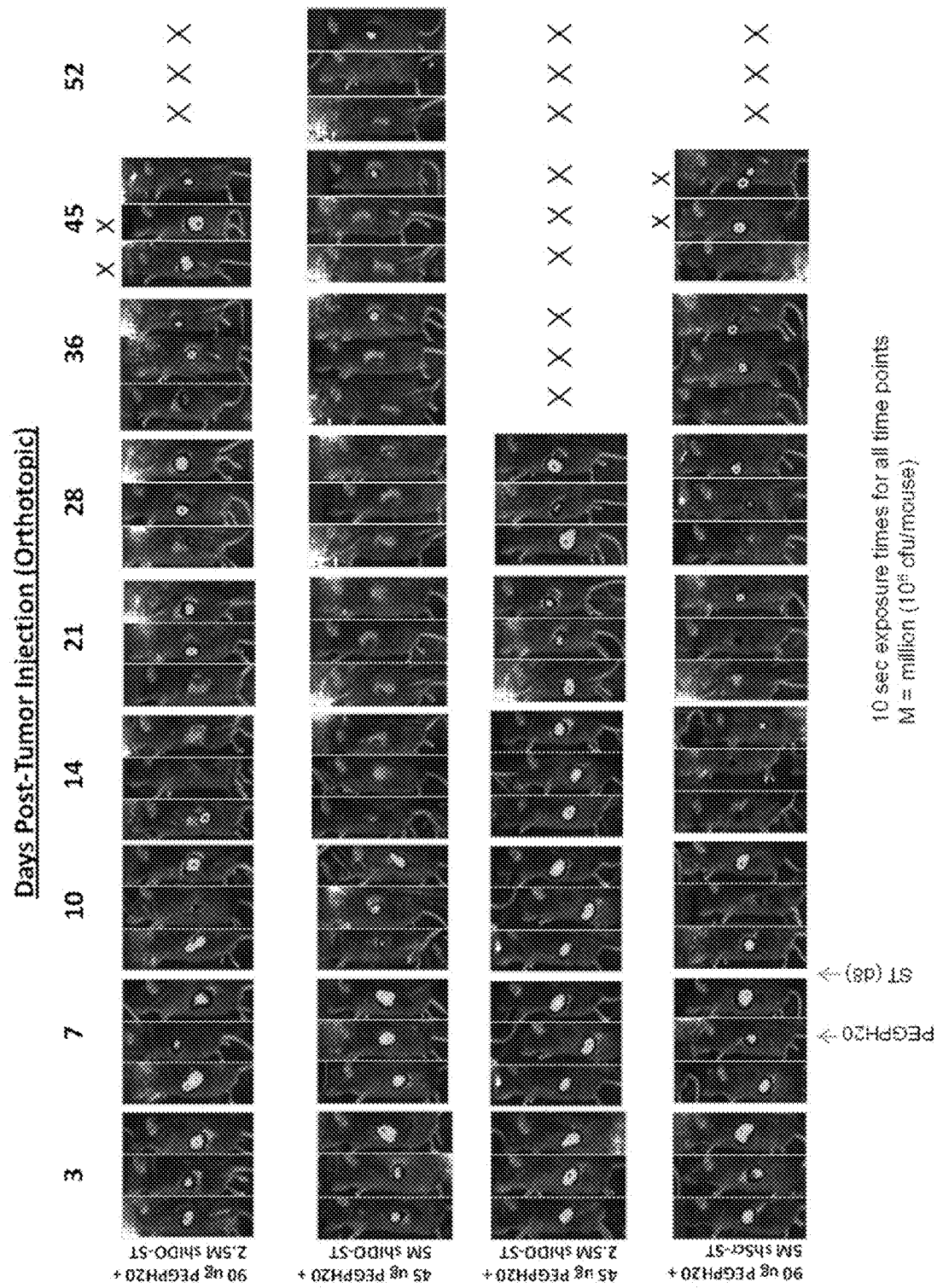
FIGS. 2A and 2B show a series of images demonstrating the effects of the combined treatment with shIDO-ST and PEGPH20™ under different dosing regimes. Mice were imaged using an intravital imaging system (IVIS) at the indicated time points after tumor implantation. The combination of shIDO-ST (5M cfu) and PEGPH20™ (45 g) resulted in controlled tumor growth and in 2 of the 3 mice complete elimination of the KPC-luc pancreatic tumors. The combination of PEGPH20™ and the control bacteria, shScr-ST also showed significant tumor growth control at early time points, but all mice eventually succumbed to tumor progression.
Figure 2B:
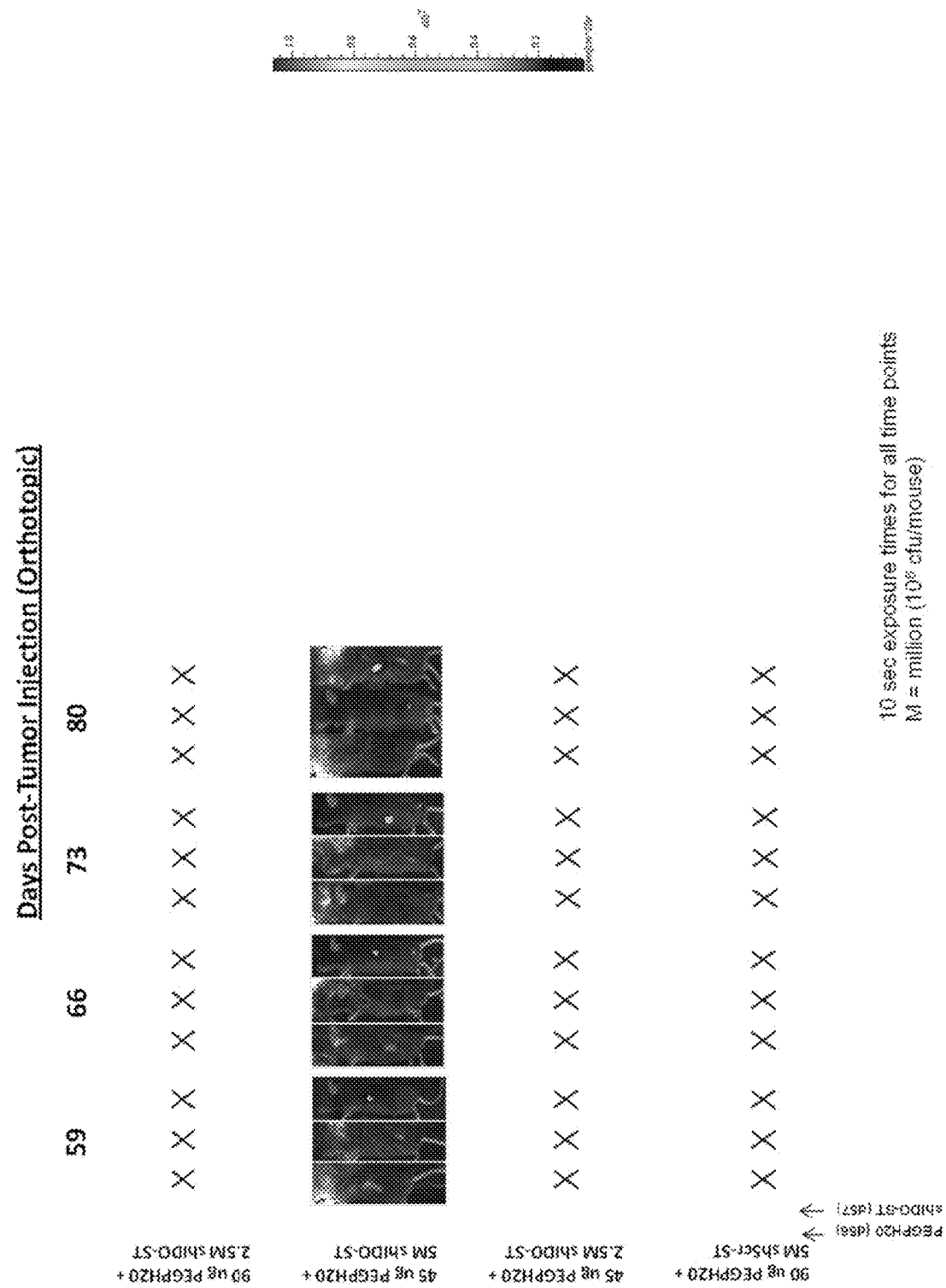
Figure 3:
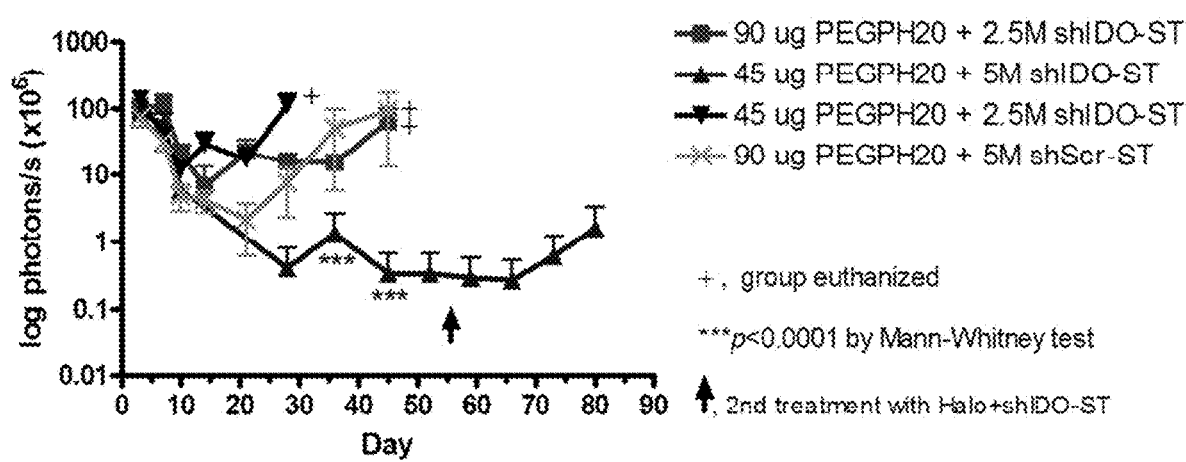
FIG. 3 is a graph showing quantitation of the IVIS for FIGS. 2A and 2B. Photons emitted from mice imaged in FIG. 2 were quantitated. Tumors from mice treated with shIDO-ST and PEGPH20™ at a specific dose of each are controlled significantly better than all other groups.

Titration of combination treatment with shIDO-ST and PEGPH20™ was performed to reduce the toxicity observed in initial experiment (FIG. 2). Three groups, representing three different dose combinations of shIDO-ST and PEGPH20™, were generated to determine optimal doses that would continue to control tumor growth with little to no toxicity. Groups consisted of full dose of PEGPH20™ (~90 ug) with half dose of shIDO-ST ($2.5\times10^6$ cfu/mouse, i.e. 2.5 million (2.5M)), half dose of PEGPH20™ with full dose of shIDO-ST, or half doses of both. A control group was added that consisted of full dose of PEGPH20™ and full dose of the scrambled (shScr-ST) control that is not specific to any gene target. As before, mice received PEGPH20™ on day 7 and shIDO-ST or shScr-ST on day 8. In this experiment, no mice were observed to become ill due to treatment using the mentioned doses. Mice receiving the full dose of PEGPH20™ with a half dose of shIDO-ST controlled tumors initially, but tumors rebounded quickly, resulting in euthanization of the group due to large tumors. The group receiving a half dose of PEGPH20™ and full dose of shIDO-ST significantly controlled tumors and in 2 of 3 mice resulted in complete cure of KPC-luc over 80 days post tumor injection. In 1 of 3 mice where tumor was still apparent, a second treatment at the same dose was given on day 56-57. Although some regression of tumor signal occurred, the tumor continued to grow as evidenced by continual increase in photon signal (FIG. 3). KPC-luc tumors in mice given half the dose of both PEGPH20™ and shIDO-ST showed no significant tumor growth control (compare to the PEGPH20™ only group in FIG. 1). The combination of PEGPH20™ with shScr-ST resulted in transient but measurable tumor growth control, however, tumors rebounded rapidly in 2 of 3 mice, and no mice were cured of KPC-luc as all mice still had tumors on day 45. Photons emitted from mice imaged in FIG. 2 were quantitated using Living Image® software. Tumors from 45 ug PEGPH20™ (PEG) and 5M shIDO-ST treated mice are controlled significantly better than all other groups (FIG. 3).

Figure 4:
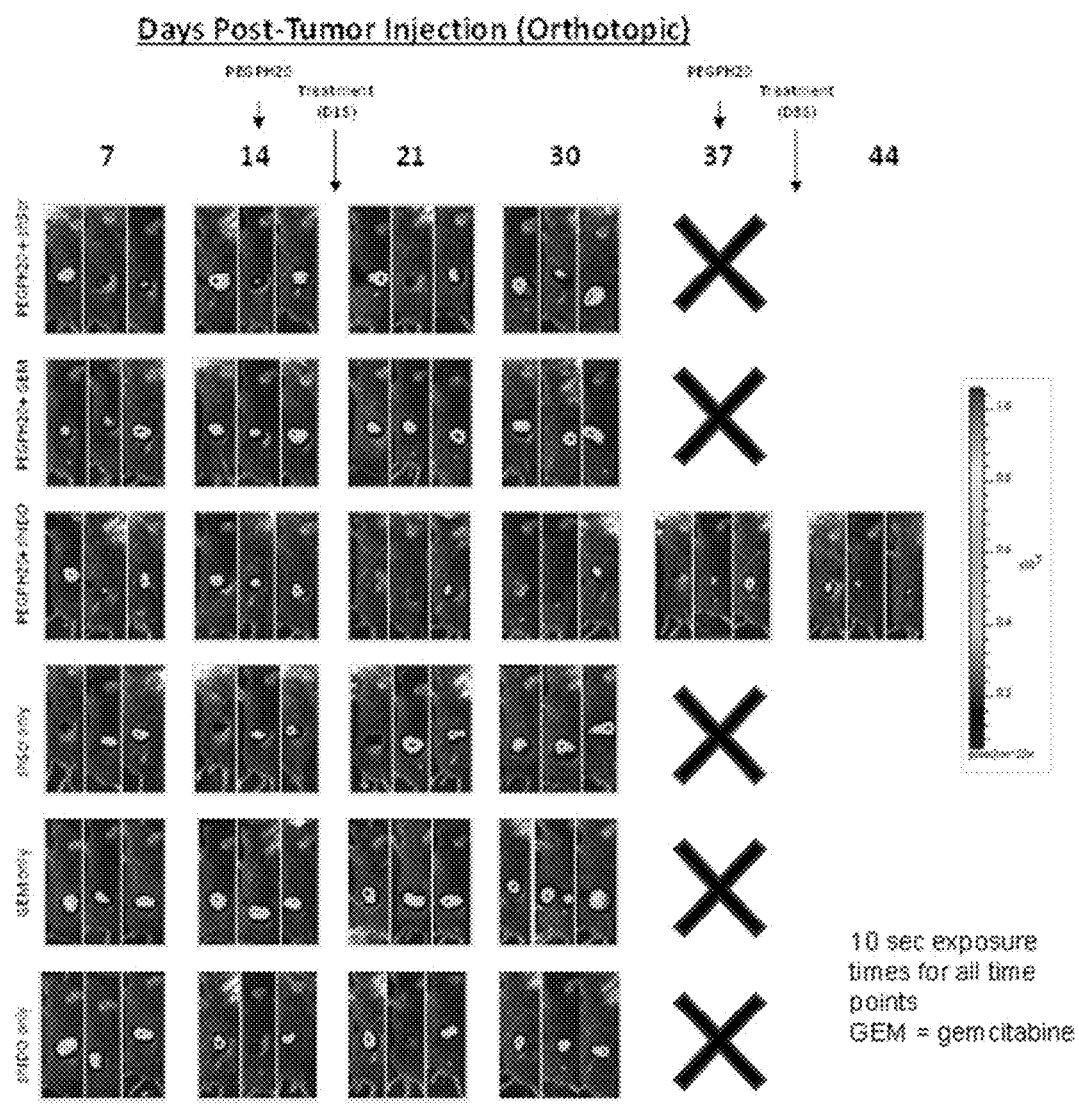
FIG. 4 shows a series of images demonstrating the effects of shIDO-ST and PEGPH20™, shScr-ST and PEGPH20™, gemcitabine and PEGPH20™ and the agents alone on KPC-luc tumors. Significant tumor reduction was observed in mice treated with shIDO-ST and PEGPH20™, while all other treatment regimens were associated with rapid tumor progression.
Figure 5:
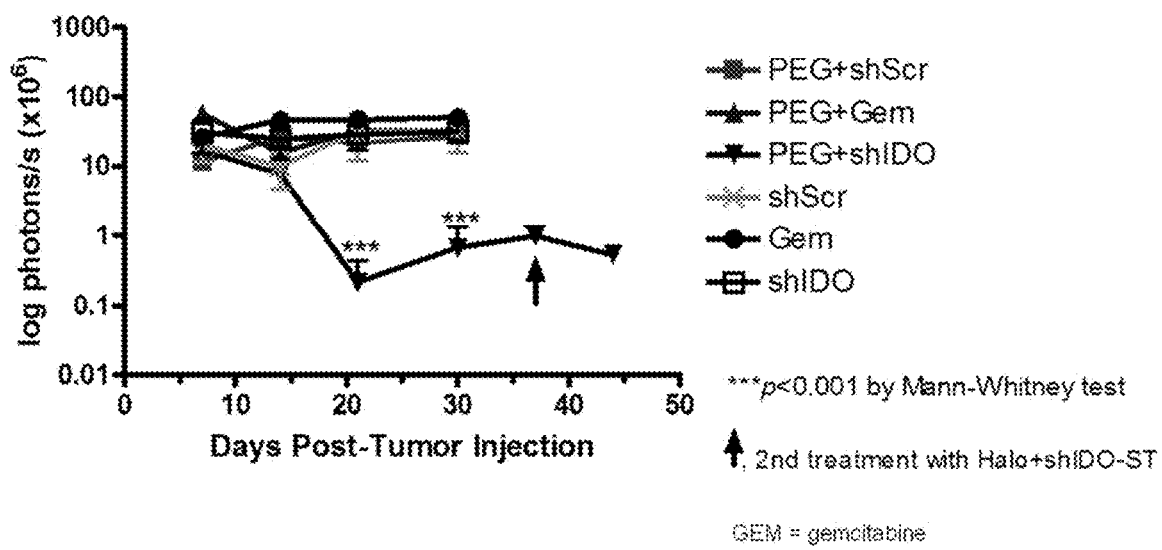
FIG. 5 is a graph showing quantitation of the IVIS for FIG. 4. Photons emitted from mice imaged in FIG. 4 were quantitated. Tumors from mice treated with shIDO-ST and PEGPH20™ are controlled significantly better than all other groups, and were alive at the conclusion of the experiment.
Figure 6:
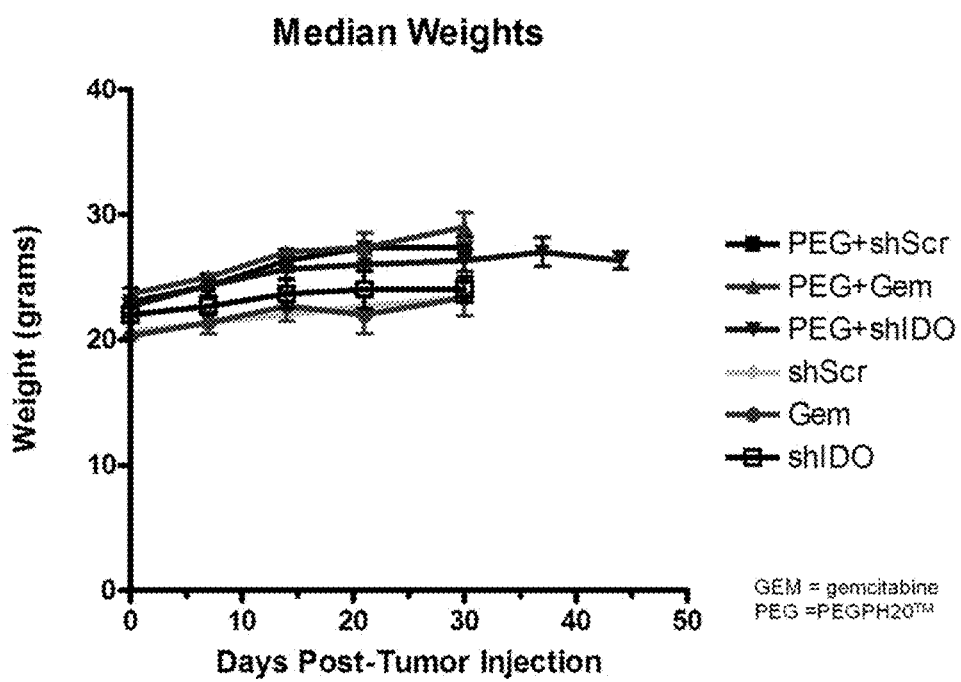
FIG. 6 is a graph showing treatment does not significantly change the weight of the mice. Mice in FIG. 4 were weighed at each imaging point. No reductions were observed in mouse weight for any group.

Due to the sensitivity of 7 day KPC-luc tumors to the combination PEGPH20™ and shScr-ST treatment (FIG. 2), treatment of implanted KPC-luc tumors was delayed to day 14. This allowed greater establishment of tumors to better compare the efficacy of shIDO-ST versus shScr-ST in combination with PEGPH20™. This experiment consisted of 6 treatment groups: 3 groups treated with PEGPH20™ and shScr-ST, shIDO-ST, or gemcitabine (GEM, at 100 mg/kg). The other 3 groups were also treated with either shScr-ST, shIDO-ST, or GEM, but with no PEGPH20™. Doses (previously determined from titration studies described in FIG. 2) consisted of 45 ug of PEGPH20™ followed by $5\times10^6$ cfu/mouse of shIDO-ST or shScr-ST. As mentioned previously, mice were started on treatment on day 14 (with PEGPH20™ or vehicle control). Mice then received a single dose of therapy on day 15. Tumor growth was visualized longitudinally by IVIS. The images are shown in FIG. 4. All groups, except for the PEGPH20™ and shIDO-ST combination group were euthanized by day 30 due to significantly large tumors causing mobility issues or illness in mice. Again, significant reduction in tumor growth was observed in 2 of 3 mice in the PEGPH20™ and shIDO-ST combination group on days 21 and 30. Although not as significant, the third mouse also exhibited tumor control which will extend survival. Tumors reappeared in mice by day 37. Therefore, a second treatment was administered to these mice to determine if this could induce further tumor regression. We saw modest tumor reduction through day 44. Photons emitted from mice imaged in FIG. 4 were quantitated using Living Image® software. Tumors from PEGPH20™ (PEG)+shIDO-ST treated mice are controlled significantly better than all other groups. See FIG. 5. Further, mice in FIG. 4 were weighed at each imaging point. There were no significant changes in mouse weight for any group. See FIG. 6.

Example 2

Combination of shArg-ST and PEGPH20™ for Cancer Treatment

To determine the effects of shArg-ST combined with PEGPH20™, five mice were orthotopically implanted with 5×10⁵ KPC-luc tumor cells. Two mice were used for the control group consisting of treatment with PEGPH20™ and a *Salmonella* (ST) therapy (shScr-ST) carrying an shRNA plasmid that does not target any known genes (Scr=scrambled). Three mice were used for the experimental group receiving PEGPH20™ and shArg-ST. All groups received PEGPH20 (90 ug/mouse intravenously) on day 7 and ST therapy on days 8 and 11 (5×10⁶ cfu/mouse, intravenously). ShScr-ST control treatment as well as shArg-ST treatment in combination with PEGPH20™ resulted in attenuation of tumor growth. However, some toxicity was observed. The results are shown in FIG. 7.

Figure 7:
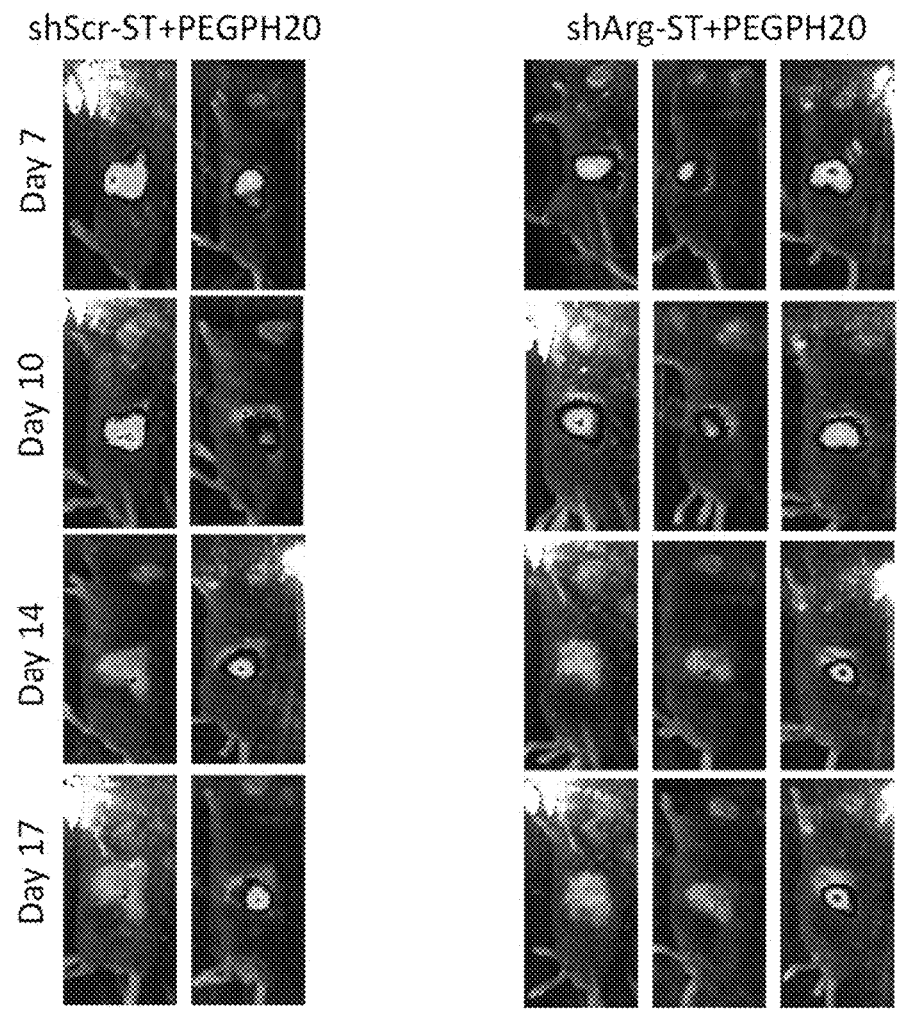
FIG. 7 shows a series of images demonstrating the effects of PEGPH20™ in combination with shArg-ST or a control shScr-ST in orthotopic KPC-luc model mice. Mice were imaged using an intravital imaging system (IVIS) at the indicated time points after tumor implantation. Tumor reduction was observed with the combined treatment of shArg-ST and PEGPH20™ and the combined treatment of shScr-ST and PEGPH20™.
Figure 8:
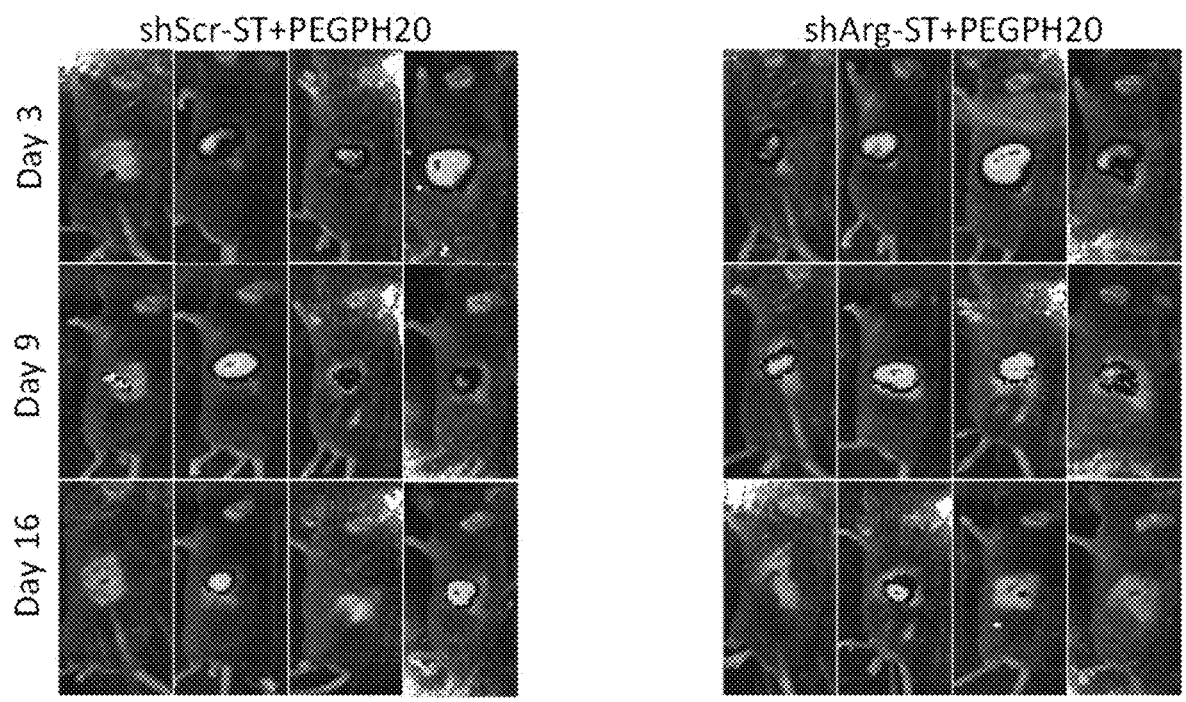
FIG. 8 shows a series of images demonstrating the effects of the combined treatment with shArg-ST and PEGPH20™ under a different dosing regime. Mice were imaged using an intravital imaging system (IVIS) at the indicated time points after tumor implantation. The combination of shIDO-ST and PEGPH20™ resulted in control of tumor growth. The combination of PEGPH20™ and the control bacteria, shScr-ST, again showed attenuation of tumor growth.

The doses used for the combination treatment with shIDO-ST and PEGPH20™ were changed to reduce the toxicity observed in the initial experiment (FIG. 7). Two groups (n=4) with orthotopic KPC-luc tumors were generated and received PEGPH20™ treatment with either shScr-ST or shArg-ST. PEGPH20™ was administered at 45 ug/mouse (half the dose than used previously) at a later time point, day 9 (as opposed to day 7 in the previous experiment), for both groups, followed by treatment with shScr-ST or shArg-ST on days 10 and 13 (at full dose, 5×10⁶ cfu). Fifty percent of mice in the control group were still cured of tumor, with the experimental group working marginally better. Mice receiving shArg-ST treatment still showed some signs of toxicity. The results are shown in FIG. 8.

Example 3

Efficacy of shIDO-ST/PEGPH20™ Combination Therapy

To further evaluate the efficacy of shIDO-ST/PEGPH20™ combination therapy, groups of mice were orthotopically implanted with 0.5 million KPC (KrasLSL.G12D/+; p53R172H/+; PdxCretg/+) cells expressing luciferase (KPC-luc cells). Fourteen days after implantation, all mice were treated with indicated therapies according to the schedule outlined in Table 1.

TABLE 1

Dose and Schedule of Administered PEGPH20 ™ and Therapeutics.

| | Dose | Schedule | Route |
|---|---|---|---|
| PEGPH20 ™ | 45 μg/mouse | (1×) d0* | Intravenous |
| shIDO-ST | 5 × 10⁶ cfu/mouse | (3×) d1-d3 | Intravenous |
| shScr-ST | 5 × 10⁶ cfu/mouse | (3×) d1-d3 | Intravenous |
| Gemcitabine | 100 mg/kg | (5×) d1-d5 | Intraperitoneal |
| Abraxane | 120 mg/kg | (3×) d1, d4, d7 | Intravenous |

*d = day.
Day 0 of treatment corresponds to day 14 post-tumor implantation.
shScr-ST is a *Salmonella* control that carries a scrambled shRNA sequence with no specificity.

Figure 9:
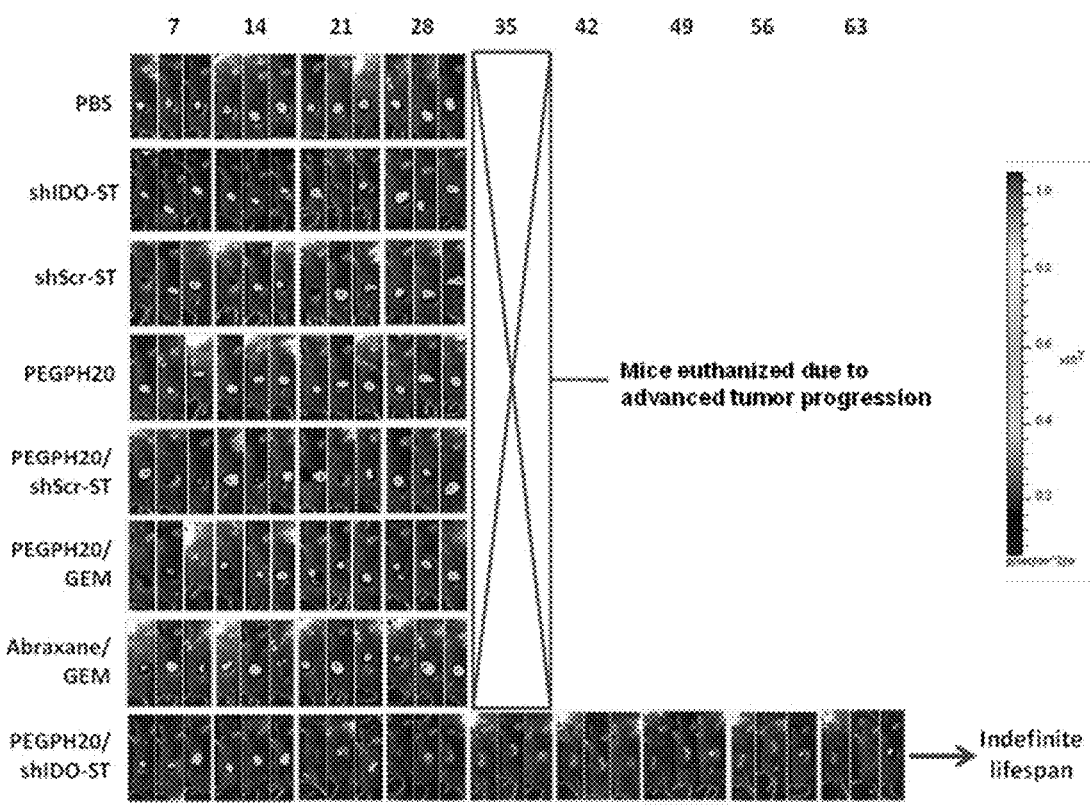
FIG. 9 shows a series of images demonstrating the effects of the combined treatment of shIDO-AT and PEGPH20™. Mice were imaged using an intravital imaging system (IVIS) at the indicated time points after tumor implantation. The combination of shIDO-ST and PEGPH20™ resulted in tumor regression and prolonged survival of the mice.

At each indicated timepoint, groups were injected with D-luciferin 5 minutes prior to imaging by intravital imaging using a Xenogen 100 machine. As shown in FIG. 9, based on the imaging results, 100% of mice treated with PEGPH20™/shIDO-ST were observed to have substantial tumor regression with nearly 75% of mice showing remarkable elimination of tumors and indefinite survival (>1 Y) comparable to that of healthy, tumor-free mice. No other treatment combinations were nearly as effective.

Figure 10:
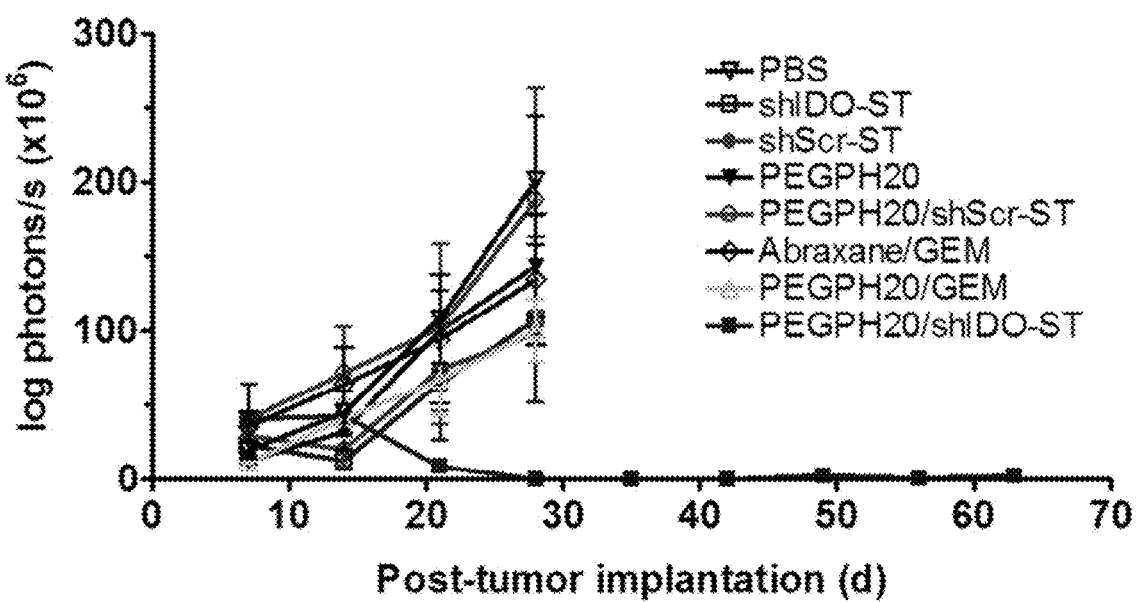
FIG. 10 is a graph of the quantitation of tumor burden at different time points post tumor implantation. Specifically, the photons emitted from IVIS imaging of the mouse groups represented in FIG. 9 were quantitated. The combination of shIDO-ST and PEGPH20™ resulted in statistically significant control of tumors while all other groups exhibited no durable control.

For statistical analyses, the photons emitted from IVIS imaging of mouse groups represented in FIG. 9 were quantitated. As shown in FIG. 10, quantitation of luciferase signal shows that only mice treated with PEGPH20™+shIDO-ST have statistically significant control of tumors (p<0.01, ANOVA) compared to all tested combinations of standard chemotherapies with PEGPH20™.

Figure 11:
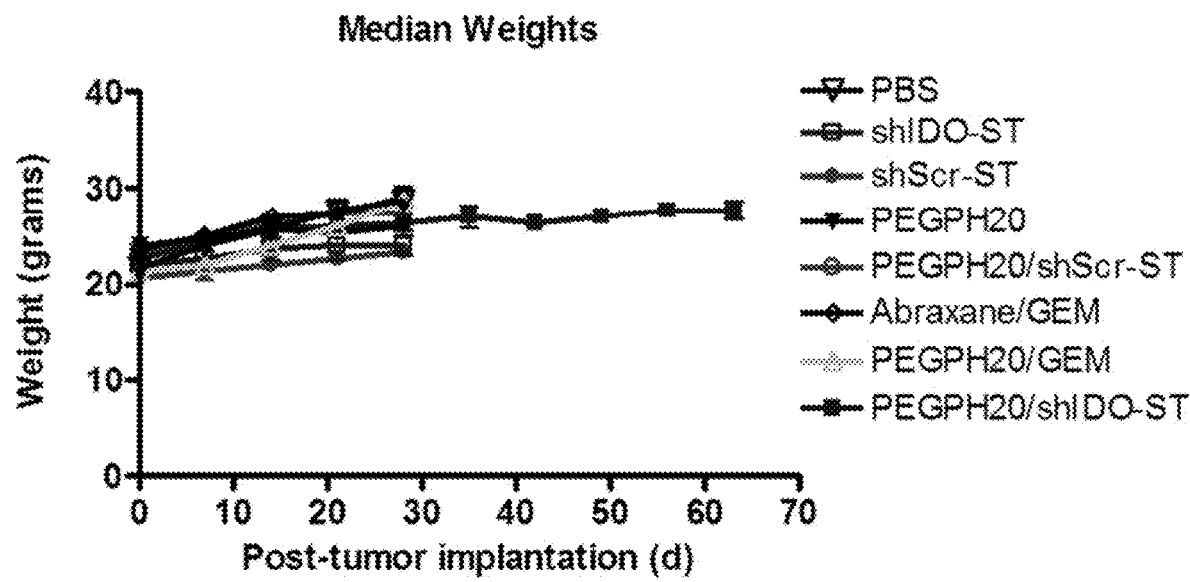
FIG. 11 is a graph showing the weight of the mouse groups represented in FIG. 9 at each time point indicated in the graph.

Mouse groups represented in FIG. 9 were weighed at each time point indicated. As shown in FIG. 11, elimination of PDAC tumors using PEGPH20™/shIDO-ST combination therapy was not associated with any significant toxicity (weight loss). Overall, no treatment group had any associated weight loss.

Figure 12:
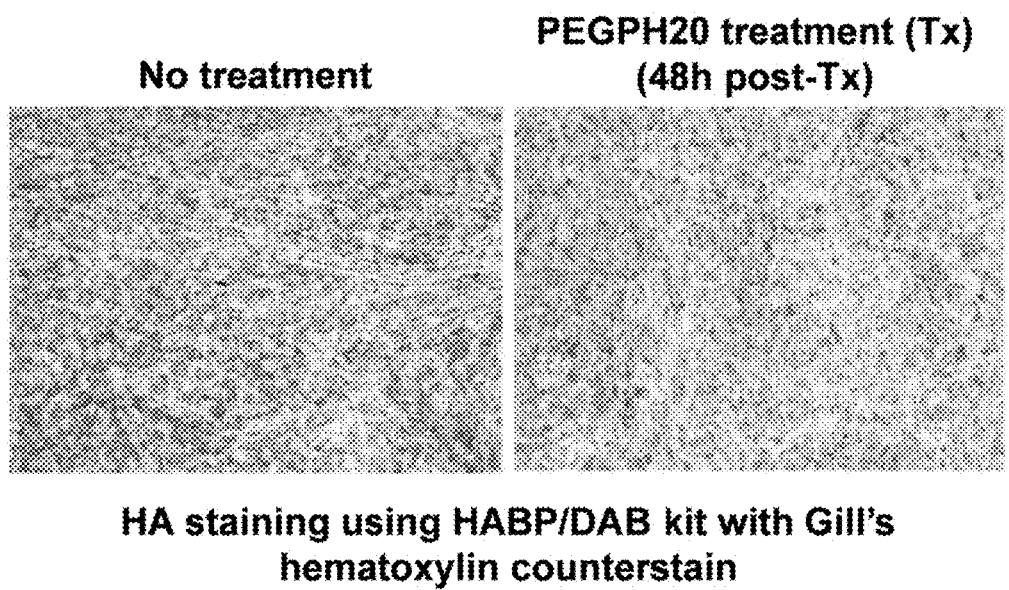
FIG. 12 shows images of hyaluronan (HA) staining of tumor bearing mice treated with PEGPH20™. Forty-eight hours after treatment with PEGPH20™, a significant depletion of hyaluronan was observed.

Fourteen day orthotopic tumors from mice untreated or treated with PEGPH20™ were fixed using a modified method (superior to standard 10% formalin fixation) that utilizes 10% acid formalin and 70% ethanol for greater intensity staining of hyaluronan (Lin et al., J Histochem Cytochem 1997). As shown in FIG. 12, the staining reveals that KPC-luc tumors 14 days after implantation express significant amounts of hyaluronan. Forty-eight hours after treatment with PEGPH20™, significant depletion of hyaluronan in sections of KPC-luc tumor tissue was observed (FIG. 12).

Figure 13:
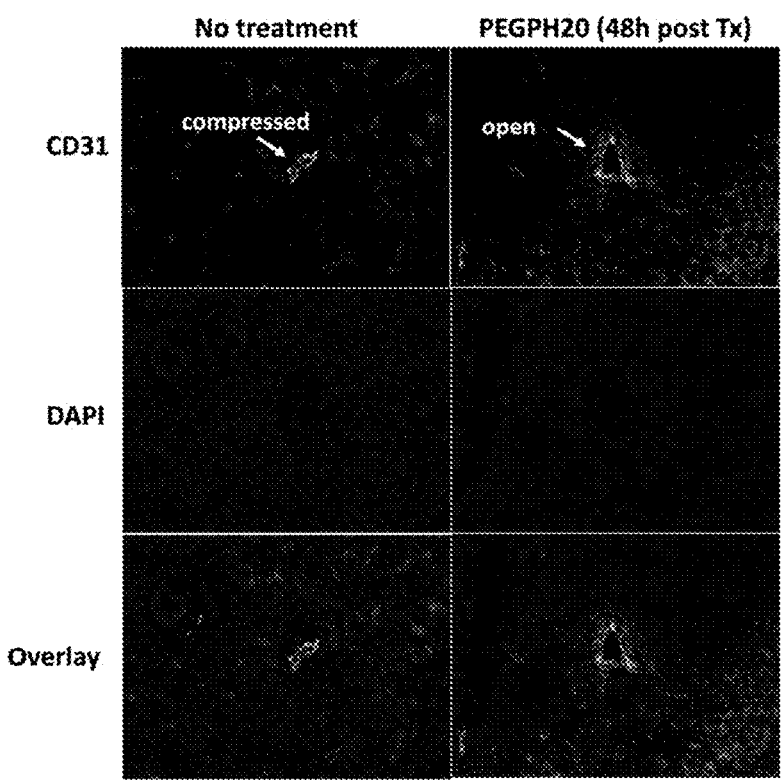
FIG. 13 shows images of open vessels in tumors in mice treated with PEGPH20™. Sections from 14 day tumors of mice untreated or treated with PEGPH20™ were stained with anti-CD31 antibody to locate cross sections of vessels within the tumor mass. Many more open vessels were observed in tumors of mice treated with PEGPH20™.

Sections from 14 day tumors of mice untreated or treated with PEGPH20 were stained with anti-CD31 antibody to locate cross sections of vessels within the tumor mass. FITC-conjugated secondary specific to CD31 primary and DAPI staining were visualized by fluorescence microscopy. As shown in FIG. 13, the images represent a majority of closed vessels in untreated tumors and many more open vessels in tumors of mice treated with PEGPH20™.

Figure 14:
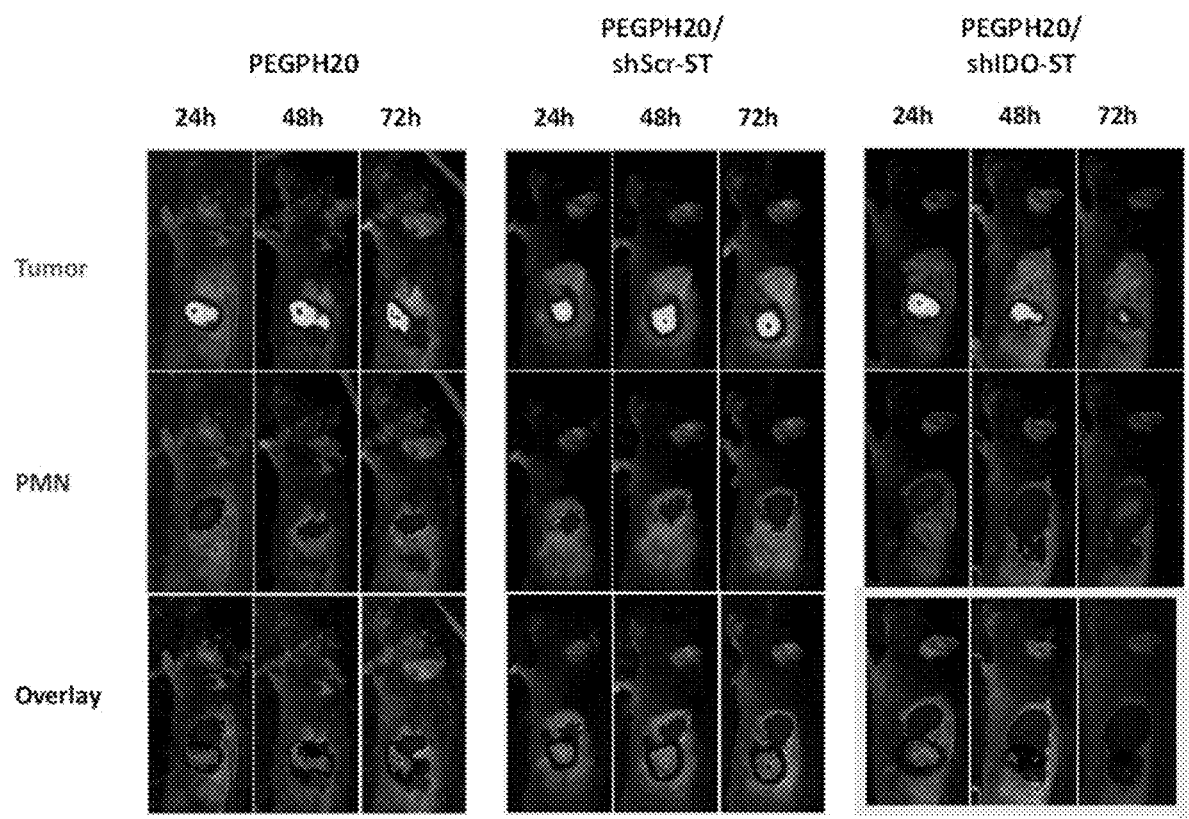
FIG. 14 shows images of the influx of *Salmonella typhimurium* (ST) and neutrophils (PMN) into tumors treated with shIDO-ST and PEGPH20™ combination therapy.

Tumor and neutrophils in indicated treatment groups were imaged over the span of 72 hours after beginning treatment with *Salmonella*. Time points represent hours after treatment with *Salmonella* (i.e. PEGPH20™ was given at −24 hour time point). As shown in FIG. 14, remarkable migration of neutrophils specifically into tumor was observed, resulting in regions of overlap, and only occurs in mice treated with PEGPH20™/shIDO-ST. Mice treated with PEGPH20™/shIDO-ST showed dramatic tumor regression coincident with PMN influx (note 72 hour time point).

Figure 15:
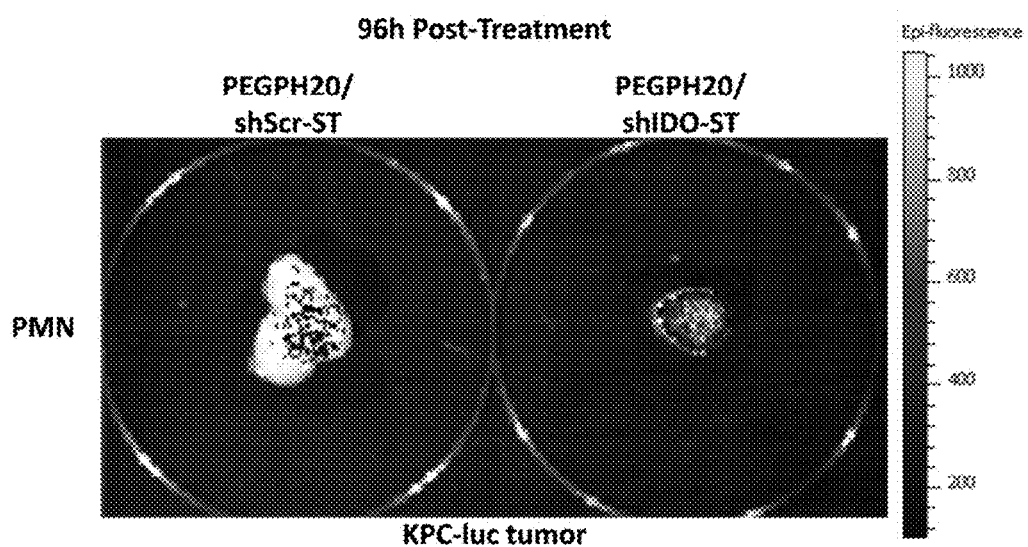
FIG. 15 shows images of surgically removed tumors analyzed for PMN 96 hours after treatment with PEGPH20™/shScr-ST or PEGPH20™/shIDO-ST.

The tumors represented in FIG. 14 for PEGPH20™/shScr-ST and PEGPH20™/shIDO-ST mice were resected 96 hours after *Salmonella* treatment to confirm presence of PMN specifically within tumor mass. Mice were injected with near infrared imaging agent (specific for PMN) 1 hour prior to tumor resection. As seen in FIG. 15, tumor resected from the PEGPH20™/shIDO-ST treated mouse (right) was observed to have significantly more PMN infiltration compared to PEGPH20/shScr-ST control treated mouse (left).

Figure 16:
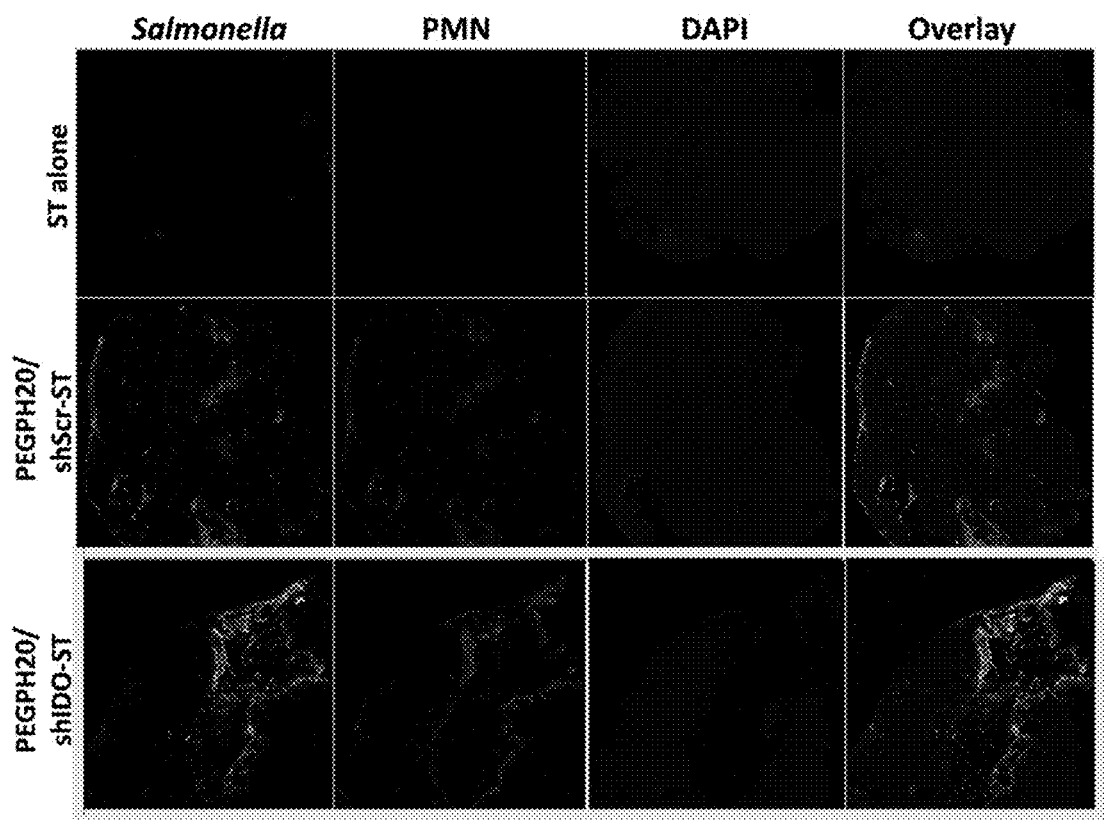
FIG. 16 shows images showing necrosis of tumor cells in the core of shIDO-ST/PEGPH20™ combination therapy treated tumors.

Control tumor and tumors represented in FIG. 15 were sectioned for immunofluorescence staining of *Salmonella*, PMN, and intact nuclei (DAPI). Only mice treated with PEGPH20™/shIDO-ST were observed to have dramatic influx of *Salmonella* and PMN (FIG. 16). PMN were observed to have significant knock down of IDO mRNA by quantitative PCR. Considerable necrosis of tumor cells (absence of DAPI staining) is visualized in core of PEGPH20™/shIDO-ST treated tumors (FIG. 16).

Figure 17:
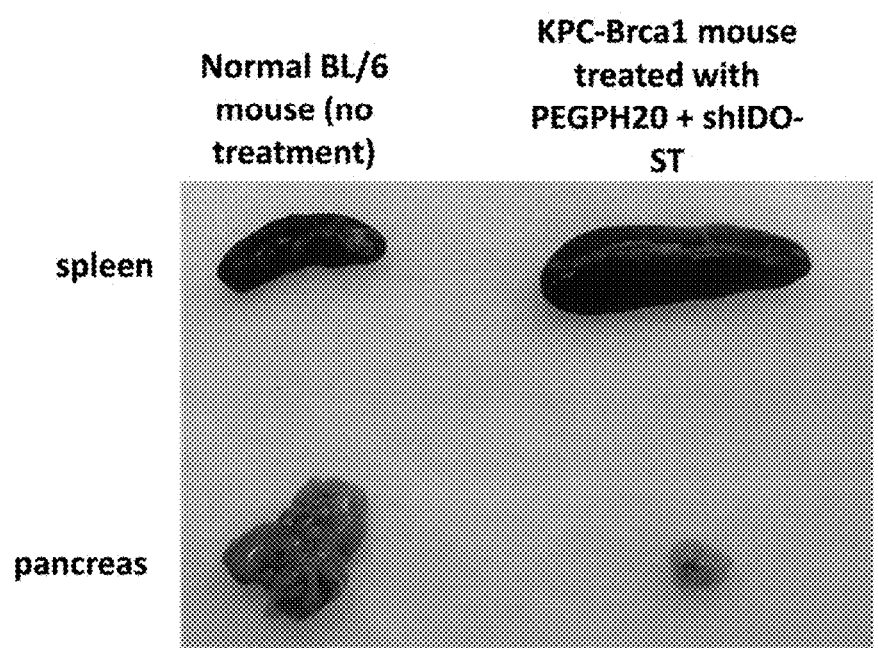
FIG. 17 shows an image of spleen and pancreas taken from normal BL/6 mice or KPC-Brca1 mice treated with shIDO-ST/PEGPH20™ combination therapy at 12 weeks.
Figure 18:
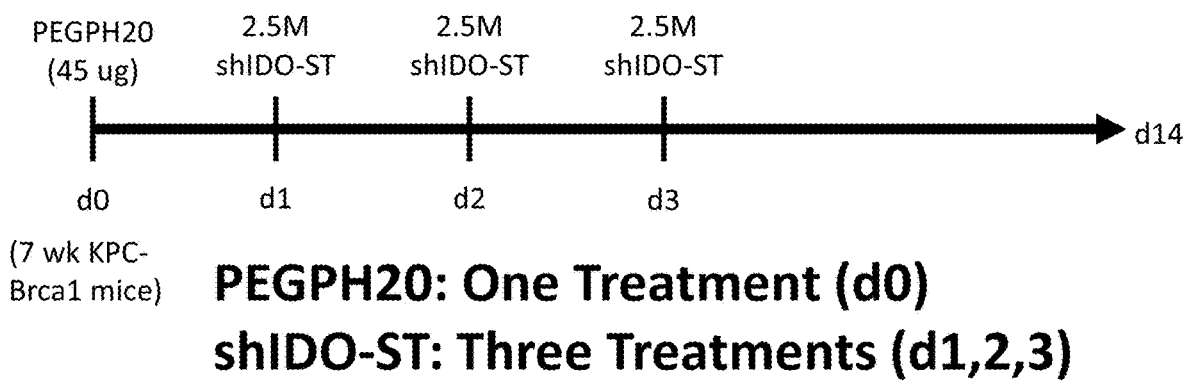
FIG. 18 shows a schematic of treatments of KPC-Brca1 mice to determine if shIDO-ST/PEGPH20™ combination therapy has efficacy in controlling spontaneous pancreatic tumors.

To further explore the effects of PEGPH20™/shIDO-ST combination treatment, a genetically engineered mouse model (GEMM) that incorporates Kras, p53, and Brca1 mutations conditionally expressed in the presence of Cre (KPC-Brca1) specifically in the pancreas, resulting in spontaneous pancreatic cancer, was treated. Spleen and pancreas on the left were extracted from a 12 week old normal C57BL/6 mouse, whereas the spleen and pancreas to the right were taken from a KPC-Brca1 mouse which was treated at 7 weeks old with PEGPH20™/shIDO-ST. The treatment schedule is outlined in FIG. 18. The treated KPC-Brca1 mouse was euthanized 5 weeks later (at 12 weeks of age). As shown in FIG. 17, the KPC-Brca1 mouse was observed to have a significantly smaller pancreas when compared to a normal sized pancreas.

Figure 19:
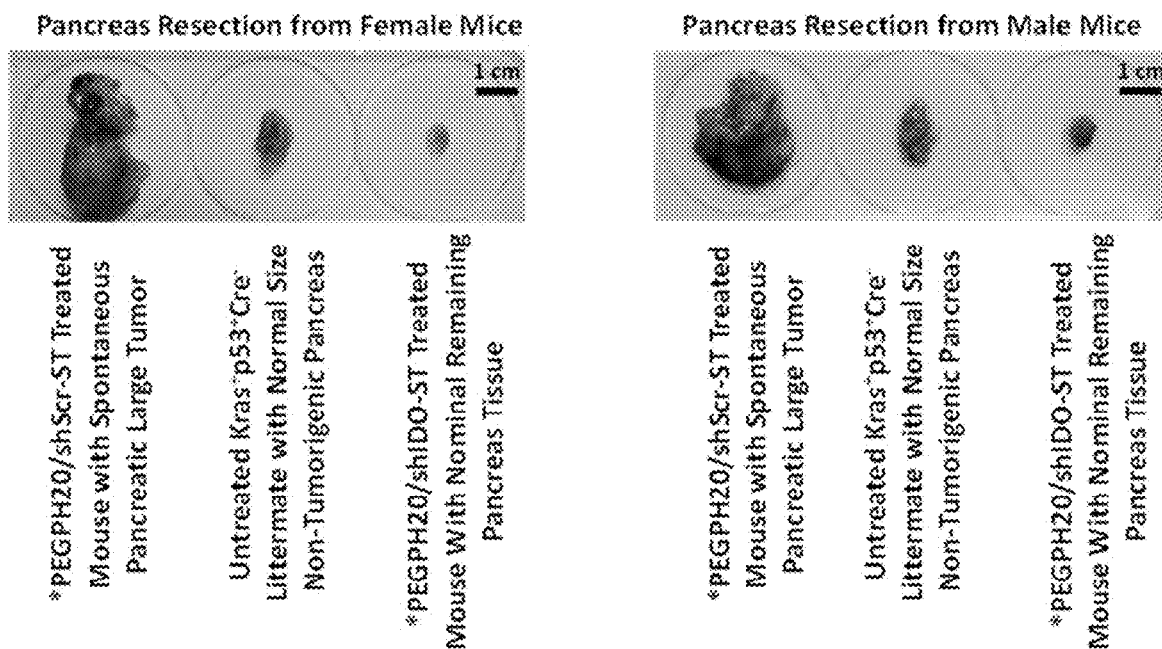
FIG. 19 shows images of the pancreas from mice treated with PEGPH20™/shScr-ST or PEGPH20™/shIDO-ST or control littermates.

Additional experiments were then performed in KPC-Brca1 mice with appropriate control treated mice (i.e. PEGPH20™/shScr-ST). Male and female KPC-Brca1 mice were treated with PEGPH20™ and either shScr-ST or shIDO-ST using the treatment schedule outlined in FIG. 18. Again, significant control/reduction in tumor size in mice treated with PEGPH20™/shIDO-ST compared to those treated with PEGPH20™/shScr-ST, indicating efficacy in a rigorous autochthonous/spontaneous model (FIG. 19).

What is claimed is:

1. A method of treating cancer in a subject comprising administering to the subject a combined effective amount of a bacterial cell and a tumor penetrating agent, wherein administration treats the cancer in the subject, wherein the tumor penetrating agent is a hyaluronidase polypeptide, wherein the combined effective amount is effective to increase tumor penetration by the bacterial cell relative to absence of the tumor penetrating agent, and wherein said tumor penetrating agent is not expressed by said bacterial cell, wherein the tumor penetrating agent is formulated in combination with a pharmaceutically acceptable carrier.

2. The method of claim 1, wherein the combined effective amount is a combined synergistic amount.

3. The method of claim 1, further comprising administering to the subject an anti-cancer agent.

4. The method of claim 3, wherein the anti-cancer agent is selected from the group consisting of a small molecule, a nucleic acid, a polypeptide, and an antibody.

5. The method of claim 1, wherein the bacterial cell is a *Salmonella* bacterial cell.

6. The method of claim 5, wherein the *Salmonella* bacterial cell is selected from the group consisting of YS1646 (ATCC #202165), RE88, LH430, SL7207, χ8429, χ8431 and χ8468.

7. The method of claim 1, wherein the bacterial cell comprises an antisense nucleic acid.

8. The method of claim 7, wherein the antisense nucleic acid targets an immunosuppressive target.

9. The method of claim 7, wherein the antisense nucleic acid is selected from the group consisting of SEQ ID NO:3-31.

10. The method of claim 8, wherein the immunosuppressive target is STAT3, IDO1, IDO2, Arginase 1, iNOS, CTLA-4, TGF-β, IL-10, pGE2 or VEGF.

11. The method of claim 1, wherein the bacterial cell is a *Salmonella* bacterial cell, a *Listeria monocytogenes* cell, a *Clostridium* bacterial cell, a *Vibrio cholera* bacterial cell, a *Shigella* bacterial cell, a *Streptococcus* bacterial cell, a *Mycobacterium bovis* bacterial cell, a *Yersinia enterocolitica* bacterial cell, a *Bacillus* bacterial cell, a *Lactobacillus* bacterial cell, a *Staphylococcus* bacterial cell, a Bifidobacteria bacterial cell or an *E. coli* bacterial cell.

12. The method of claim 1, wherein the bacterial cell is a *Salmonella choleraesuis* bacterial cell, a *Salmonella typhimurium* bacterial cell, a *Salmonella enteritidis* bacterial cell, a *Salmonella typhi* bacterial cell, a *Salmonella enterica* bacterial cell, a *Clostridium histolyticus* bacterial cell, *Clostridium novyi* bacterial cell, *Streptococcus* pyrogenes bacterial cell, a *Streptococcus gordonii* bacterial cell, or a *Bacillus anthracis* bacterial cell.

13. A method of stimulating an immune system in a subject comprising administering to the subject a combined effective amount of a bacterial cell and a tumor penetrating agent, wherein administration of the bacterial cell and the tumor penetrating agent stimulates the immune system of the subject, wherein the tumor penetrating agent is a hyaluronidase polypeptide, and wherein the combined effective amount is effective to increase tumor penetration by the bacterial cell relative to absence of the tumor penetrating agent, wherein said tumor penetrating agent is not expressed by said bacterial cell, wherein the tumor penetrating agent is formulated in combination with a pharmaceutically acceptable carrier.

14. The method of claim 13, wherein the immune response is an anti-cancer immune response.

* * * * *

UNITED STATES PATENT AND TRADEMARK OFFICE
CERTIFICATE OF CORRECTION

| | | |
|---|---|---|
| PATENT NO. | : 11,141,492 B2 | |
| APPLICATION NO. | : 14/978590 | |
| DATED | : October 12, 2021 | |
| INVENTOR(S) | : Don J. Diamond and Edwin Manuel | |

It is certified that error appears in the above-identified patent and that said Letters Patent is hereby corrected as shown below:

In the Specification

At Column 1, Line 11, the following heading and paragraph are inserted:
--STATEMENT AS TO RIGHTS OF INVENTIONS MADE UNDER FEDERALLY SPONSORED RESEARCH AND DEVELOPMENT
This invention was made with government support under R21 CA174306 awarded by the National Institutes of Health. The government has certain rights in the invention.--

Signed and Sealed this
Twenty-fourth Day of September, 2024

Katherine Kelly Vidal
*Director of the United States Patent and Trademark Office*

SEQUENCE LISTING

```
<160> NUMBER OF SEQ ID NOS: 31

<210> SEQ ID NO 1
<211> LENGTH: 509
<212> TYPE: PRT
<213> ORGANISM: Homo Sapiens

<400> SEQUENCE: 1

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300

Arg Ile Val Phe Thr Asp Gln Val Leu Lys Phe Leu Ser Gln Asp Glu
305                 310                 315                 320
```

```
Leu Val Tyr Thr Phe Gly Glu Thr Val Ala Leu Gly Ala Ser Gly Ile
            325                 330                 335
Val Ile Trp Gly Thr Leu Ser Ile Met Arg Ser Met Lys Ser Cys Leu
        340                 345                 350
Leu Leu Asp Asn Tyr Met Glu Thr Ile Leu Asn Pro Tyr Ile Ile Asn
            355                 360                 365
Val Thr Leu Ala Ala Lys Met Cys Ser Gln Val Leu Cys Gln Glu Gln
370                 375                 380
Gly Val Cys Ile Arg Lys Asn Trp Asn Ser Asp Tyr Leu His Leu
385                 390                 395                 400
Asn Pro Asp Asn Phe Ala Ile Gln Leu Glu Lys Gly Gly Lys Phe Thr
            405                 410                 415
Val Arg Gly Lys Pro Thr Leu Glu Asp Leu Glu Gln Phe Ser Glu Lys
        420                 425                 430
Phe Tyr Cys Ser Cys Tyr Ser Thr Leu Ser Cys Lys Glu Lys Ala Asp
            435                 440                 445
Val Lys Asp Thr Asp Ala Val Asp Val Cys Ile Ala Asp Gly Val Cys
    450                 455                 460
Ile Asp Ala Phe Leu Lys Pro Pro Met Glu Thr Glu Pro Gln Ile
465                 470                 475                 480
Phe Tyr Asn Ala Ser Pro Ser Thr Leu Ser Ala Thr Met Phe Ile Val
            485                 490                 495
Ser Ile Leu Phe Leu Ile Ile Ser Ser Val Ala Ser Leu
            500                 505

<210> SEQ ID NO 2
<211> LENGTH: 511
<212> TYPE: PRT
<213> ORGANISM: Homo Sapiens

<400> SEQUENCE: 2

Met Gly Val Leu Lys Phe Lys His Ile Phe Phe Arg Ser Phe Val Lys
1               5                   10                  15
Ser Ser Gly Val Ser Gln Ile Val Phe Thr Phe Leu Leu Ile Pro Cys
            20                  25                  30
Cys Leu Thr Leu Asn Phe Arg Ala Pro Pro Val Ile Pro Asn Val Pro
        35                  40                  45
Phe Leu Trp Ala Trp Asn Ala Pro Ser Glu Phe Cys Leu Gly Lys Phe
    50                  55                  60
Asp Glu Pro Leu Asp Met Ser Leu Phe Ser Phe Ile Gly Ser Pro Arg
65                  70                  75                  80
Ile Asn Ala Thr Gly Gln Gly Val Thr Ile Phe Tyr Val Asp Arg Leu
            85                  90                  95
Gly Tyr Tyr Pro Tyr Ile Asp Ser Ile Thr Gly Val Thr Val Asn Gly
            100                 105                 110
Gly Ile Pro Gln Lys Ile Ser Leu Gln Asp His Leu Asp Lys Ala Lys
        115                 120                 125
Lys Asp Ile Thr Phe Tyr Met Pro Val Asp Asn Leu Gly Met Ala Val
    130                 135                 140
Ile Asp Trp Glu Glu Trp Arg Pro Thr Trp Ala Arg Asn Trp Lys Pro
145                 150                 155                 160
Lys Asp Val Tyr Lys Asn Arg Ser Ile Glu Leu Val Gln Gln Gln Asn
            165                 170                 175
Val Gln Leu Ser Leu Thr Glu Ala Thr Glu Lys Ala Lys Gln Glu Phe
            180                 185                 190
```

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asn Trp Asn Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Trp
                485                 490                 495

Arg Leu Glu Val Trp Asp Gln Gly Ile Ser Arg Ile Gly Phe Phe
            500                 505                 510

<210> SEQ ID NO 3
<211> LENGTH: 29
<212> TYPE: DNA
<213> ORGANISM: Artificial Sequence
<220> FEATURE:
<223> OTHER INFORMATION: Synthetic Construct

<400> SEQUENCE: 3
agttcctggc accttggatt gagagtcaa                                    29

<210> SEQ ID NO 4
<211> LENGTH: 29
<212> TYPE: DNA
<213> ORGANISM: Artificial Sequence
<220> FEATURE:

<223> OTHER INFORMATION: Synthetic Construct

<400> SEQUENCE: 4
actggataac ttcattagca gaatctcaa                                    29

<210> SEQ ID NO 5
<211> LENGTH: 29
<212> TYPE: DNA
<213> ORGANISM: Artificial Sequence
<220> FEATURE:
<223> OTHER INFORMATION: Synthetic Construct

<400> SEQUENCE: 5
catcaatcct gtggtataac atgctgacc                                    29

<210> SEQ ID NO 6
<211> LENGTH: 29
<212> TYPE: DNA
<213> ORGANISM: Artificial Sequence
<220> FEATURE:
<223> OTHER INFORMATION: Synthetic Construct

<400> SEQUENCE: 6
acctgaagac caagttcatc tgtgtgaca                                    29

<210> SEQ ID NO 7
<211> LENGTH: 19
<212> TYPE: DNA
<213> ORGANISM: Artificial Sequence
<220> FEATURE:
<223> OTHER INFORMATION: Synthetic Construct

<400> SEQUENCE: 7
cctcgcaata gtagatact                                               19

<210> SEQ ID NO 8
<211> LENGTH: 19
<212> TYPE: DNA
<213> ORGANISM: Artificial Sequence
<220> FEATURE:
<223> OTHER INFORMATION: Synthetic Construct

<400> SEQUENCE: 8
cgtctctcta ttggtggaa                                               19

<210> SEQ ID NO 9
<211> LENGTH: 19
<212> TYPE: DNA
<213> ORGANISM: Artificial Sequence
<220> FEATURE:
<223> OTHER INFORMATION: Synthetic Construct

<400> SEQUENCE: 9
gcaaagaatc tcctgcaga                                               19

<210> SEQ ID NO 10
<211> LENGTH: 19
<212> TYPE: DNA
<213> ORGANISM: Artificial Sequence
<220> FEATURE:
<223> OTHER INFORMATION: Synthetic Construct

<400> SEQUENCE: 10
gcccatgaca tacgagaac                                               19

<210> SEQ ID NO 11
<211> LENGTH: 19
<212> TYPE: DNA
<213> ORGANISM: Artificial Sequence
<220> FEATURE:
<223> OTHER INFORMATION: Synthetic Construct

<400> SEQUENCE: 11
ccagtccgtg agtttgtca                                                19

<210> SEQ ID NO 12
<211> LENGTH: 19
<212> TYPE: DNA
<213> ORGANISM: Artificial Sequence
<220> FEATURE:
<223> OTHER INFORMATION: Synthetic Construct

<400> SEQUENCE: 12
gcagttcctt tctggtatg                                                19

<210> SEQ ID NO 13
<211> LENGTH: 18
<212> TYPE: DNA
<213> ORGANISM: Artificial Sequence
<220> FEATURE:
<223> OTHER INFORMATION: Synthetic Construct

<400> SEQUENCE: 13
gcctttgttg atgtccct                                                 18

<210> SEQ ID NO 14
<211> LENGTH: 19
<212> TYPE: DNA
<213> ORGANISM: Artificial Sequence
<220> FEATURE:
<223> OTHER INFORMATION: Synthetic Construct

<400> SEQUENCE: 14
ccagggactg actacctta                                                19

<210> SEQ ID NO 15
<211> LENGTH: 19
<212> TYPE: DNA
<213> ORGANISM: Artificial Sequence
<220> FEATURE:
<223> OTHER INFORMATION: Synthetic Construct

<400> SEQUENCE: 15
gccaaagaca tcgtgtaca                                                19

<210> SEQ ID NO 16
<211> LENGTH: 18
<212> TYPE: DNA
<213> ORGANISM: Artificial Sequence
<220> FEATURE:
<223> OTHER INFORMATION: Synthetic Construct

<400> SEQUENCE: 16
tctctacatc acagaaga                                                 18

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct

<400> SEQUENCE: 17
gtattgtact attgtggact a                     21

<210> SEQ ID NO 18
<211> LENGTH: 21
<212> TYPE: DNA
<213> ORGANISM: Artificial Sequence
<220> FEATURE:
<223> OTHER INFORMATION: Synthetic Construct

<400> SEQUENCE: 18
ccagtattat ggctccttta a                     21

<210> SEQ ID NO 19
<211> LENGTH: 21
<212> TYPE: DNA
<213> ORGANISM: Artificial Sequence
<220> FEATURE:
<223> OTHER INFORMATION: Synthetic Construct

<400> SEQUENCE: 19
gccacagcaa tataggctca t                     21

<210> SEQ ID NO 20
<211> LENGTH: 21
<212> TYPE: DNA
<213> ORGANISM: Artificial Sequence
<220> FEATURE:
<223> OTHER INFORMATION: Synthetic Construct

<400> SEQUENCE: 20
cctatctcca ttctactact a                     21

<210> SEQ ID NO 21
<211> LENGTH: 21
<212> TYPE: DNA
<213> ORGANISM: Artificial Sequence
<220> FEATURE:
<223> OTHER INFORMATION: Synthetic Construct

<400> SEQUENCE: 21
gctgtaacaa aggaaataga a                     21

<210> SEQ ID NO 22
<211> LENGTH: 21
<212> TYPE: DNA
<213> ORGANISM: Artificial Sequence
<220> FEATURE:
<223> OTHER INFORMATION: Synthetic Construct

<400> SEQUENCE: 22
cgcagttatg agctttctta a                     21

<210> SEQ ID NO 23
<211> LENGTH: 21
<212> TYPE: DNA
<213> ORGANISM: Artificial Sequence
<220> FEATURE:
<223> OTHER INFORMATION: Synthetic Construct

<400> SEQUENCE: 23
ccgcagttat gagctttctt a                     21

<210> SEQ ID NO 24
<211> LENGTH: 21

```
<212> TYPE: DNA
<213> ORGANISM: Artificial Sequence
<220> FEATURE:
<223> OTHER INFORMATION: Synthetic Construct

<400> SEQUENCE: 24
cctgggataa aggctcttgt t                                              21

<210> SEQ ID NO 25
<211> LENGTH: 21
<212> TYPE: DNA
<213> ORGANISM: Artificial Sequence
<220> FEATURE:
<223> OTHER INFORMATION: Synthetic Construct

<400> SEQUENCE: 25
gaaagctatc acatatctga a                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic Construct

<400> SEQUENCE: 26
ctttggaaag ctatcacata t                                              21

<210> SEQ ID NO 27
<211> LENGTH: 21
<212> TYPE: DNA
<213> ORGANISM: Artificial Sequence
<220> FEATURE:
<223> OTHER INFORMATION: Synthetic Construct

<400> SEQUENCE: 27
ccattgtctt tggaaagcta t                                              21

<210> SEQ ID NO 28
<211> LENGTH: 21
<212> TYPE: DNA
<213> ORGANISM: Artificial Sequence
<220> FEATURE:
<223> OTHER INFORMATION: Synthetic Construct

<400> SEQUENCE: 28
cttcttccag attctctgaa a                                              21

<210> SEQ ID NO 29
<211> LENGTH: 21
<212> TYPE: DNA
<213> ORGANISM: Artificial Sequence
<220> FEATURE:
<223> OTHER INFORMATION: Synthetic Construct

<400> SEQUENCE: 29
gcttcaagct catgtggaca a                                              21

<210> SEQ ID NO 30
<211> LENGTH: 21
<212> TYPE: DNA
<213> ORGANISM: Artificial Sequence
<220> FEATURE:
<223> OTHER INFORMATION: Synthetic Construct

<400> SEQUENCE: 30
```

```
caaggaatct tgcccttcca t                                              21

<210> SEQ ID NO 31
<211> LENGTH: 21
<212> TYPE: DNA
<213> ORGANISM: Artificial Sequence
<220> FEATURE:
<223> OTHER INFORMATION: Synthetic Construct

<400> SEQUENCE: 31
gcagtgccat tgtctttgga a                                              21
```